United States Patent [19]

Yumoto et al.

[11] Patent Number: 5,652,082
[45] Date of Patent: Jul. 29, 1997

[54] PHOTOSENSITIVE BIS (HALOMETHYLOXADIAZOLE) COMPOUND AND PHOTOSENSITIVE TRANSFER SHEET USING THE SAME

[75] Inventors: Masatoshi Yumoto; Naoto Yanagihara; Ken Iwakura; Juniti Fujimori; Shinji Fujimoto; Minoru Maeda, all of Shizuoaka, Japan

[73] Assignee: Fuji Photo Film Co., Ltd., Kanagawa, Japan

[21] Appl. No.: 703,090

[22] Filed: Aug. 26, 1996

Related U.S. Application Data

[62] Division of Ser. No. 524,031, Sep. 6, 1995, Pat. No. 5,576,441.

[30] Foreign Application Priority Data

| Sep. 6, 1994 | [JP] | Japan | 6-212794 |
| Sep. 22, 1994 | [JP] | Japan | 6-227984 |
| Feb. 27, 1995 | [JP] | Japan | 7-38743 |
| Feb. 28, 1995 | [JP] | Japan | 7-40261 |

[51] Int. Cl.$^6$ ............................. F23Q 1/02
[52] U.S. Cl. ...................... 430/270.1; 430/283.1
[58] Field of Search ................ 430/270.1, 283.1

[56] References Cited

U.S. PATENT DOCUMENTS

| 3,954,475 | 5/1976 | Bonham et al. | 96/67 |
| 3,987,037 | 10/1976 | Bonham et al. | 260/240 |
| 4,189,323 | 2/1980 | Buhr et al. | 430/281 |
| 5,374,642 | 12/1994 | Kardoff et al. | 514/363 |

FOREIGN PATENT DOCUMENTS

| 62-58241 | 3/1987 | Japan | G03C 1/68 |

*Primary Examiner*—Robert Gerstl
*Attorney, Agent, or Firm*—Sughrue, Mion, Zinn, Macpeak & Seas

[57] ABSTRACT

Photosensitive bis(halomethyloxadiazole) compounds which are capable of producing free radicals upon exposure to light represented by the following general formulae (1) to (4):

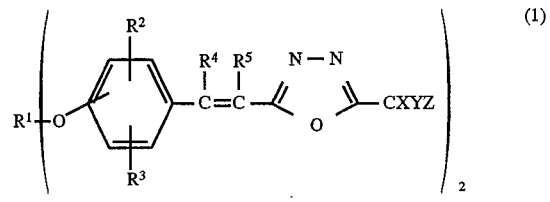

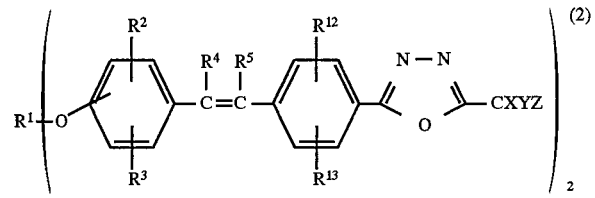

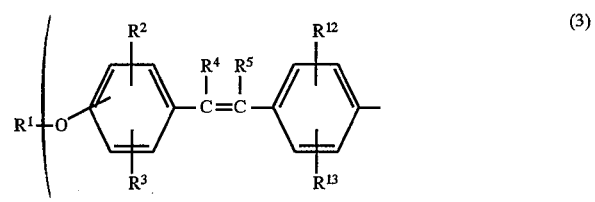

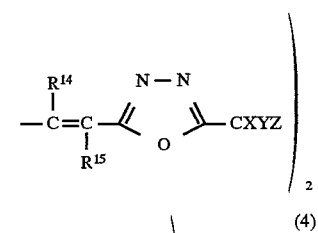

The symbols in the above formulae are defined in the present specification. The photosensitive bis(halomethyloxadiazole) compound is useful in the fields of recording materials such as photosensitive protecting films, printing plates, photoresists, proofs, etc. Furthermore, a photosensitive transfer sheet using a photosensitive composition containing the photosensitive bis(halomethyloxadiazole) is useful in making a prepress proof for color proofing, a color display, etc.

2 Claims, No Drawings

PHOTOSENSITIVE BIS (HALOMETHYLOXADIAZOLE) COMPOUND AND PHOTOSENSITIVE TRANSFER SHEET USING THE SAME

This is a divisional application No. 08/524,031 filed Sep. 6, 1995, now U.S. Pat. No. 5,576,441.

FIELD OF THE INVENTION

The present invention relates to a novel photosensitive bis(halomethyloxadiazole) compound capable of producing free radicals upon exposure to light. The photosensitive bis(halomethyloxadiazole) compound is useful in the fields of recording materials such as photosensitive protecting films, printing plates, photoresists, proofs, etc. Furthermore, the present invention relates to a photosensitive transfer sheet for use in making a prepress proof for color proofing, a color display or the like.

BACKGROUND OF THE INVENTION

Compounds capable of forming free radicals by photolysis upon exposure to light (free radical forming agent) are well known in the fields of graphic arts and photosensitive recording materials. Such compounds are widely used as a photoradical polymerization initiator in a photopolymerizable composition, as a photoactivator in a free radical photographic composition, and as a photoinitiator in reactions in which an acid produced by exposure to light catalyze. Various photosensitive materials useful in recording systems such as printing, reproduction, duplication and so on, are prepared using the free radical generating agents.

Bis(trihalomethyl)-s-triazine compounds are proposed as halogen free radical generating agents which are sensitive to light of wavelengths ranging from near ultraviolet to visible region. Such compounds are described in detail, e.g., in U.S. Pat. Nos. 3,954,475, 3,987,037 and 4,189,323, and JP-A-62-58241 (the term "JP-A" as used herein means an "unexamined published Japanese patent application"). Although those compounds are sensitive to light having a wavelength of from near ultraviolet to visible region, they have a problem that their decomposition products upon exposure tend to generate a pale yellow stain, and further, in such a system that a photoradical polymerization initiator or decomposition products thereof remain in a recording layer, a yellow stain due to photolysis generates upon storage under daylight. These phenomena are severe problems in the field such as a color proof, in which a minute change of color tone makes a defect.

As a result of our intensive studies on the above described problems, the inventors have found compounds having excellent properties.

SUMMARY OF THE INVENTION

An object of the present invention is to provide photosensitive bis(halomethyloxadiazole) compounds which are sensitive to light having a wavelength of from near ultraviolet to visible region, with the sensitivities being high, and generate no color stain due to the decomposition upon exposure and during storage under daylight.

Another object of the present invention is to provide a photosensitive transfer sheet using the photosensitive bis (halomethyloxadiazole) compounds which generates no color stain.

The above objects of the present invention is achieved by providing:

photosensitive bis(halomethyloxadiazole) compounds represented by one of the following general formulae (1) to (4):

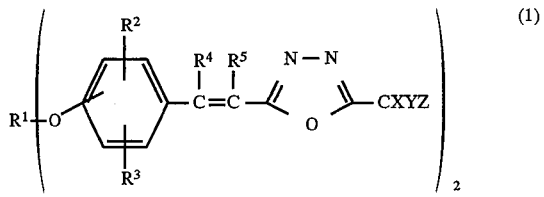

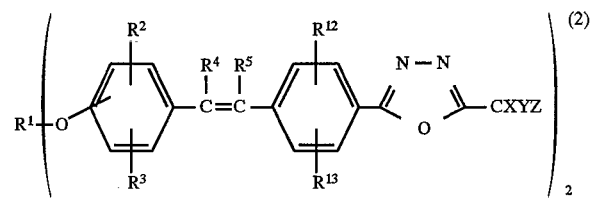

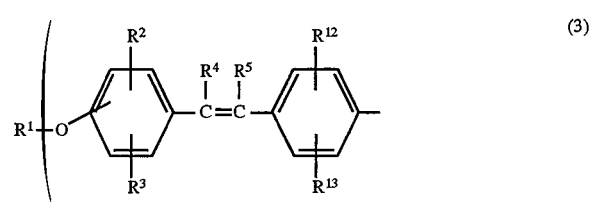

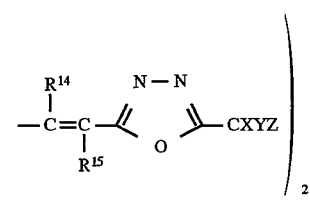

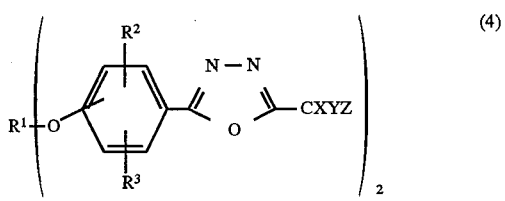

wherein $R^1$ represents $-CO-R^6-CO-$, $-C_nH_{2n}-$, or $-C_nH_{2n}-R^7-C_nH_{2n}-$; n represents an integer of from 1 to 20; $R^2$, $R^3$, $R^{12}$ and $R^{13}$ are the same or different, and each represents a hydrogen atom, an alkyl group containing 1 to 10 carbon atoms, an alkoxy group containing 1 to 10 carbon atoms, an acyloxy group containing 2 to 10 carbon atoms, or a halogen atom; $R^4$, $R^5$, $R^{14}$ and $R^{15}$ are the same or different, and each represents a hydrogen atom, an alkyl group containing 1 to 10 carbon atoms, an unsubstituted phenyl group, or a substituted phenyl group substituted with an alkyl or alkoxy group containing 1 to 6 carbon atoms or a halogen atom; X, Y and Z are the same or different, and each represents a hydrogen atom or a halogen atom, providing that all of X, Y and Z cannot be hydrogen atoms simultaneously; $R^6$ represents $-C_mH_{2m}-$ or $-OC_mH_{2m}O-$; m represents an integer of from 2 to 20; $R^7$ represents $-O-$, $-S-$, $-N(R^8)-$, $-SO_2-$, $-O-SO-O-$, $-O-CO-R^9-CO-O-$, $-SO_2-R^9-SO_2-$, $-CO-R^9-CO-$, or $-O-R^{10}-O-$; $R^8$ represents an alkyl group containing 1 to 10 carbon atom, an unsubstituted phenyl group, or a substituted phenyl group substituted with an alkyl or alkoxy group containing 1 to 6 carbon atoms or a halogen atom; $R^9$ represents $-C_lH_{2l}-$, —$C_lH_{2l}$O—$R^{11}$—O$C_lH_{2l}$—, —NH$C_kH_{2k}$NH—, —NH$C_kH_{2k-2}$NH—, —NHCH$_2$—C$_6$H$_4$—CH$_2$NH—, —O$C_kH_{2k}$O—, or —C$_6$H$_4$—; l represents an integer of from 1 to 20; k represents an integer of from 2 to 20; $R^{10}$ represents —$C_pH_{2p}$— or —$C_pH_{2p}$—O—$R^{11}$—O$C_pH_{2p}$—; p represents an integer of from 2 to 20; $R^{11}$ represents —C$_6$H$_4$—$C_qH_{2q}$—C$_6$H$_4$—, —C$_6$H$_4$—S—C$_6$H$_4$—, —C$_6$H$_4$—SO$_2$—C$_6$H$_4$—, —C$_6$H$_4$—, —C$_6$H$_4$—O—C$_6$H$_4$—, —C$_6$H$_4$—C(CF$_3$)$_2$—C$_6$H$_4$— or —C$_6$H$_4$—C$_6$H$_4$—; and q represents an integer of from 2 to 10; and a photosensitive transfer sheet comprising a support having thereon (a) a peeling layer containing an organic polymer and (b) a photopolymerizable photosensitive resin layer containing a photosensitive resin and a photopolymerization initiator, in this order, wherein the photopolymerization initiator comprises at least one photosensitive bis(halomethyloxadiazole) compound represented by one of the foregoing general formulae (1) to (4).

DETAILED DESCRIPTION OF THE INVENTION

The photosensitive bis(halomethyloxadiazole) compounds relating to the present invention are compounds having structures formed by dimerizing hitherto known photosensitive halomethyloxadiazole compounds. Examples of known photosensitive halomethyloxadiazole compounds are described, e.g., in U.S. Pat. Nos. 4,212,970, 4,232,106, 4,279,982, and 4,701,399, EP-A-237233, JP-B-03-42462 (the term "JP-B" as used herein means an "examined Japanese Patent Publication"), JP-A-60-138539, JP-A-60-239473, JP-A-60-241049, JP-A-04-328550, JP-A-04-362644, JP-A-05-45875 and JP-A-05-66558. The photosensitive bis(halomethyloxadiazole) compounds relating to the present invention include all of the bis compounds prepared by employing the above described photosensitive halomethyloxadiazoles as basic mother nuclei and combined with each other by a certain linkage group.

Of these bis compounds, the compounds represented by one of the following formulae (1) to (4) are preferred:

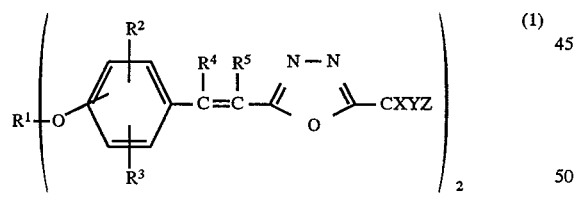

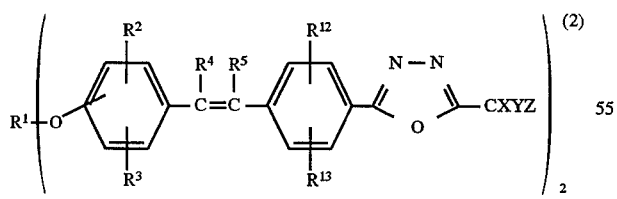

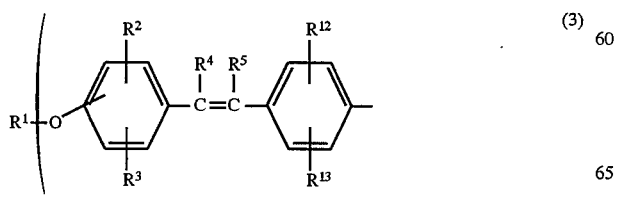

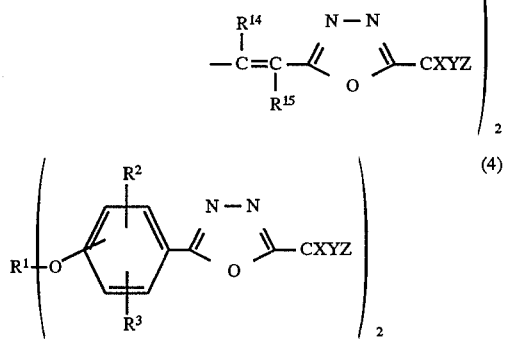

wherein $R^1$ represents —CO—$R^6$—CO—, —$C_nH_{2n}$—, or —$C_nH_{2n}$—$R^7$—$C_nH_{2n}$—, n represents an integer of from 1 to 20; $R^2$, $R^3$, $R^{12}$ and $R^{13}$ are the same or different, and each represents a hydrogen atom, an alkyl group containing 1 to 10 carbon atoms, an alkoxy group containing 1 to 10 carbon atoms, an acyloxy group containing 2 to 10 carbon atoms, or a halogen atom; $R^4$, $R^5$, $R^{14}$ and $R^{15}$ are the same or different, and each represents a hydrogen atom, an alkyl group containing 1 to 10 carbon atoms, an unsubstituted phenyl group, or a substituted phenyl group substituted with an alkyl or alkoxy group containing 1 to 6 carbon atoms or a halogen atom; X, Y and Z are the same or different, and each represents a hydrogen atom or a halogen atom, providing that all of X, Y and Z cannot be hydrogen atoms simultaneously; $R^6$ represents —$C_mH_{2m}$— or —O$C_mH_{2m}$O—; m represents an integer of from 2 to 20; $R^7$ represents —O—, —S—, —N($R^8$)—, —SO$_2$—, —O—SO—O—, —O—CO—$R^9$—CO—O—, —SO$_2$—$R^9$—SO$_2$—, —CO—$R^9$—CO—, or —O—$R^{10}$—O—; $R^8$ represents an alkyl group containing 1 to 10 carbon atom, an unsubstituted phenyl group, or a substituted phenyl group substituted with an alkyl or alkoxy group containing 1 to 6 carbon atoms or a halogen atom; $R^9$ represents —$C_lH_{2l}$—, —$C_lH_{2l}$O—$R^{11}$—O$C_lH_{2l}$—, —NH$C_kH_{2k}$NH—, —NH$C_kH_{2k-2}$NH—, —NHCH$_2$—C$_6$H$_4$—CH$_2$NH—, —O$C_kH_{2k}$O—, or —C$_6$H$_4$—; l represents an integer of from 1 to 20; k represents an integer of from 2 to 20; $R^{10}$ represents —$C_pH_{2p}$— or —$C_pH_{2p}$—O—$R^{11}$—O$C_pH_{2p}$—; p represents an integer of from 2 to 20; $R^{11}$ represents —C$_6$H$_4$—$C_qH_{2q}$—C$_6$H$_4$—, —C$_6$H$_4$—S—C$_6$H$_4$—, —C$_6$H$_4$—SO$_2$—C$_6$H$_4$—, —C$_6$H$_4$—, —C$_6$H$_4$—O—C$_6$H$_4$—, —C$_6$H$_4$—C(CF$_3$)$_2$—C$_6$H$_4$— or —C$_6$H$_4$—C$_6$H$_4$—; and q represents an integer of from 2 to 10.

In general formulae (1) to (4), $R^1$ is preferably —CO—$R^6$—CO—, —$C_nH_{2n}$— or —$C_nH_{2n}$—$R^7$—$C_nH_{2n}$—, in which n represents an integer of from 1 to 12. The formula "—$C_nH_{2n}$—" as used herein includes both straight and branched alkylene groups.

$R^2$, $R^3$, $R^{12}$ and $R^{13}$ may be the same or different, and each of them is preferably a hydrogen atom, an alkyl group containing 1 to 5 carbon atoms, an alkoxy group containing 1 to 5 carbon atoms, an acyloxy group containing 2 to 5 carbon atoms, a chlorine atom or a bromine atom.

$R^4$, $R^5$, $R^{14}$ and $R^{15}$ may be the same or different, and each of them is preferably a hydrogen atom, an alkyl group containing 1 to 5 carbon atoms or a phenyl group.

As for the combination of X, Y and Z, CCl$_3$, CBr$_3$ or CHCl$_2$ is preferable in the form of CXYZ.

In general formulae (1) to (4), $R^6$ is preferably —$C_mH_{2m}$— or —$OC_mH_{2m}O$—, in which m represents an integer of from 2 to 12. The formula "$C_mH_{2m}$—" as used herein includes both straight and branched alkylene groups.

$R^7$ is preferably —O—, —S—, —$SO_2$—, —O—SO—O—, —O—CO—$R^9$—CO—O—, —CO—$R^9$—CO—, or —O—$R^{10}$—O—, and more preferably —O—, —S—, —O—SO—O—, —O—CO—$R^9$—CO—O— or —CO—$R^9$—CO—.

$R^8$ is preferably an alkyl group containing 1 to 8 carbon atoms, an unsubstituted phenyl group or a substituted phenyl group substituted with an alkyl or alkoxy group containing 1 to 4 carbon atoms or a halogen atom.

$R^9$ is preferably —$C_lH_{2l}$—, —$C_lH_{2l}O$—$R^{11}$—$OC_lH_{2l}$—, —$NHC_kH_{2k}NH$—, —$NHC_kH_{2k-2}NH$—, —$OC_kH_{2k}O$— or —$C_6H_4$—, in which l is an integer of from 1 to 18 and k is an integer of from 2 to 12, and more preferably —$C_lH_{2l}$—, —$C_lH_{2l}O$—$R^{11}$—$OC_lH_{2l}$—, —$NHC_kH_{2k}NH$—, —$NHC_kH_{2k-2}NH$—, —$OC_kH_{2k}O$—, in which l is an integer of from 1 to 16 and k is an integer of from 3 to 10. The formulae "$C_lH_{2l}$—" and "$C_kH_{2k}$" as used herein include both straight and branched alkylene groups.

$R^{10}$ is preferably —$C_pH_{2p}$— or —$C_pH_{2p}$—O—$R^{11}$—$OC_pH_{2p}$—, wherein p is an integer of from 2 to 12. The formula "—$C_pH_{2p}$—" as used herein include both straight and branched alkylene groups.

$R^{11}$ is preferably —$C_6H_4$—$C_qH_{2q}$—$C_6H_4$—, in which q is an integer of from 2 to 6, —$C_6H_4$— or —$C_6H_4$—O—$C_6H_4$—, and more preferably —$C_6H_4$—$C_qH_{2q}$—$C_6H_4$—, in which q is an integer of from 2 to 5. The formula "—$C_qH_{2q}$—" as used herein include both straight and branched alkylene groups.

In general formulae (1) to (4), $R^1$ is particularly preferably —CO—$C_mH_{2m}$—CO—, —$C_nH_{2n}$—, —$C_nH_{2n}$—O—SO—O—$C_nH_{2n}$—, —$C_nH_{2n}$—O—CO—$C_lH_{2l}$—CO—O—$C_nH_{2n}$—, —$C_nH_{2n}$—O—CO—$C_lH_{2l}O$—$C_6H_4$—$C_qH_{2q}$—$C_6H_4$—$OC_lH_{2l}$—CO—O—$C_nH_{2n}$—, —$C_nH_{2n}$—O—CO—$NHC_kH_{2k}NH$—CO—O—$C_nH_{2n}$—, —$C_nH_{2n}$—O—CO—$NHC_kH_{2k-2}NH$—CO—O—$C_nH_{2n}$—, —$C_nH_{2n}$—CO—$OC_kH_{2k}O$—CO—$C_nH_{2n}$— and —$C_nH_{2n}$—CO—$NHC_kH_{2k}NH$—CO—$C_nH_{2n}$—, in which m is an integer of from 2 to 10, n is an integer of from 1 to 8, l is an integer of from 1 to 16, q is an integer of from 3 to 5, and k is an integer of from 3 to 10.

Of the compounds represented by general formula (1), compounds represented by the following general formulae (5) to (11) are preferred:

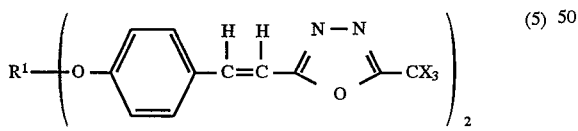

(5)

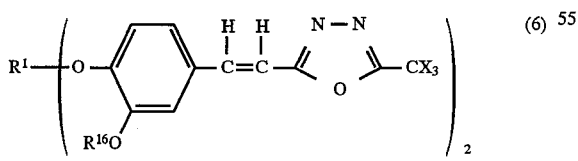

(6)

wherein $R^{16}$ is an alkyl group

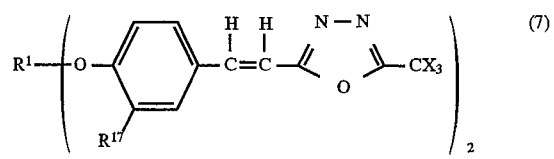

(7)

wherein $R^{17}$ is an alkyl group

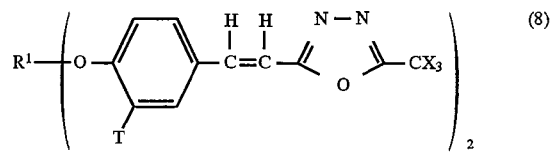

(8)

wherein T is a chlorine or bromine atom

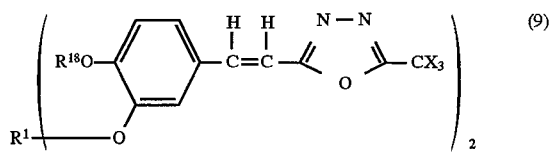

(9)

wherein $R^{18}$ is an alkyl group

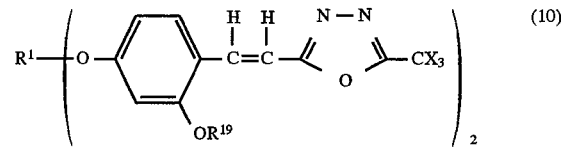

(10)

wherein $R^{19}$ is an alkyl group

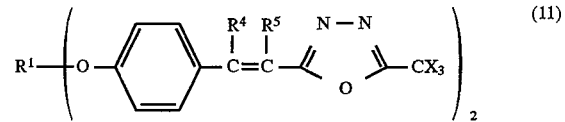

(11)

Of the compounds represented by general formula (2), compounds represented by the following general formulae (12) and (13) are preferred:

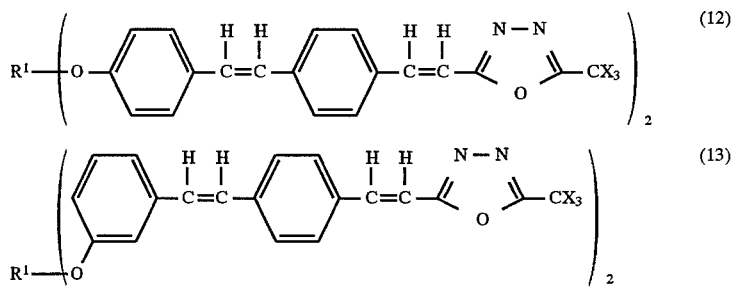

Of the compounds represented by general formula (3), compounds represented by the following general formulae (14) and (15) are preferred:

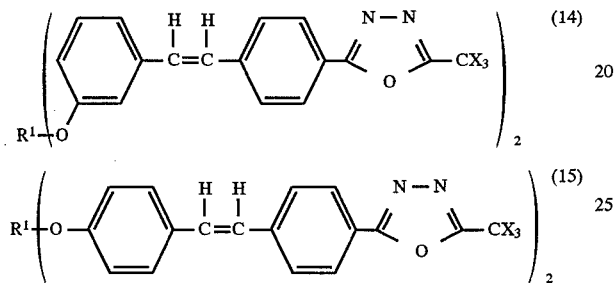

Of the compounds represented by general formula (4), compounds represented by the following general formulae (16) to (20) are preferred:

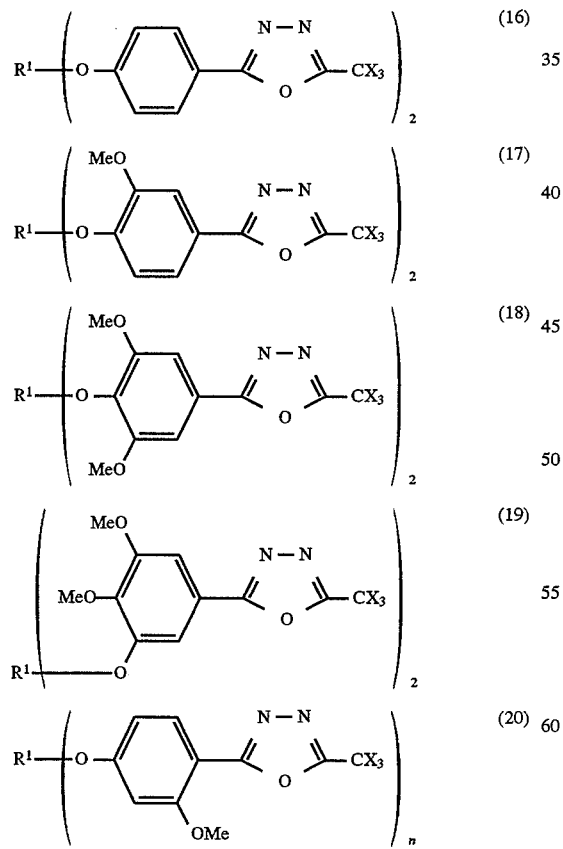

Specific examples of a group represented by $R^1$ in each of the general formulae (1) to (4) are described below:

$-C_4H_8-$, $-C_5H_{10}-$, $-C_6H_{12}-$,
$-C_8H_{16}-$, $-CH_{10}H_{20}-$, $-COC_2H_4CO-$,
$-COC_4H_8CO-$, $-COC_6H_{12}CO-$,
$-C_2H_4O-SO-OCH_2H_4-$,
$-C_2H_4OCOC_2H_4COOC_2H_4-$,
$-C_2H_4OCOC_4H_8COOC_2H_4-$,
$-C_2H_4OCOC_6H_{12}COOC_2H_4-$,
$-C_2H_4OCOC_8H_{16}COOC_2H_4-$,
$-C_2H_4OCOC_{16}H_{32}COOC_2H_4-$,
$-C_3H_6OCOC_2H_4COOC_3H_6-$,
$-C_3H_6OCOC_4H_8COOC_3H_6-$,
$-C_3H_6OCOC_5H_{12}COOC_3H_6-$,
$-C_3H_6OCOC_8H_{16}COOC_3H_6-$,
$-C_4H_8OCOC_2H_4COOC_4H_8-$,
$-C_4H_8OCOC_4H_8COOC_4H_8-$,
$-C_4H_8OCOC_6H_{12}COOC_4H_8-$,
$-C_4H_8OCOC_8H_{16}COOC_4H_8-$,
$-C_2H_4OCOOC_6H_{12}OCOOC_2H_4-$,
$-C_2H_4OC_2H_4OC_2H_4-$, $-C_2H_4OC_2H_4-$,
$-C_3H_6OC_3H_6-$, $-C_2H_4SC_2H_4-$,
$-C_2H_4N(Me)C_2H_4-$,
$-C_3H_6COC_2H_4COC_3H_6-$,
$-C_2H_4SO_2C_2H_4-$,
$-CH_2COOC_2H_4OCOCH_2-$,
$-CH_2COOC_4H_8OCOCH_2-$,
$-CH_2COOC_5H_{10}OCOCH_2-$,
$-CH_2COOC_6H_{12}OCOCH_2-$,
$-CH_2COOC_8H_{16}OCOCH_2-$,
$-C_2H_4COOC_4H_8OCOC_2H_4-$,
$-C_2H_4COOC_8H_{16}OCOC_2H_4-$,
$-C_3H_6COOC_4H_8OCOC_3H_6-$,
$-C_3H_6COOC_8H_{16}OCOC_3H_6-$,
$-CH_2CONHC_2H_4NHCOC_2-$,

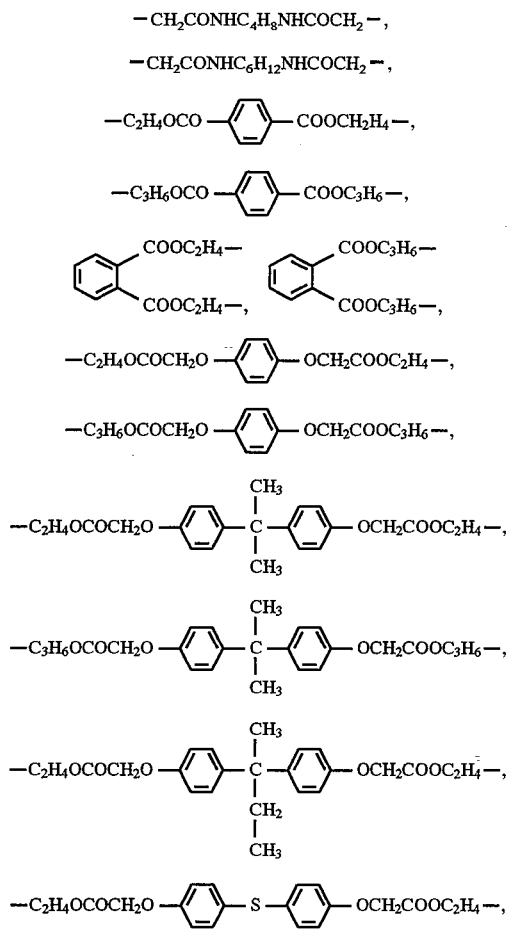

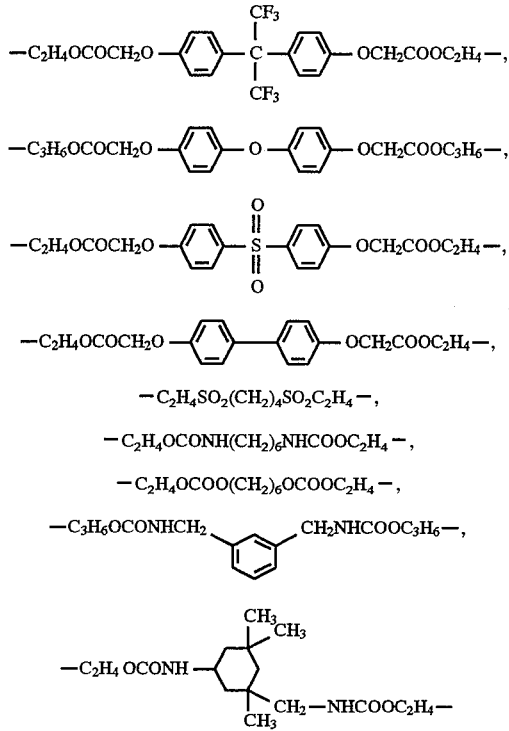

Specific examples of photosensitive bis(halomethyloxadiazole) compounds of the present invention are described below, wherein the specific examples are exemplified with lisiting various examples of $R^1$ (and $R^4$ and $R^5$ in some examples). However, the invention should not be construed as being limited to these examples.

| Example Nos. | $-R^1-$ | $R^4$ | $R^5$ |
|---|---|---|---|

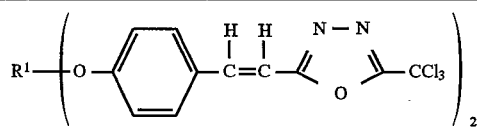

| | | | |
|---|---|---|---|
| 1 | $-(CH_2)_2-$ | | |
| 2 | $-(CH_2)_3-$ | | |
| 3 | $-\underset{\underset{CH_3}{\mid}}{CH}CH_2-$ | | |
| 4 | $-\underset{\underset{C_2H_5}{\mid}}{CH}CH_2-$ | | |
| 5 | $-(CH_2)_5-$ | | |
| 6 | $-\underset{\underset{CH_3}{\mid}}{CH}CH_2CH_2CH_2-$ | | |
| 7 | $-CH_2\underset{\underset{CH_3}{\mid}}{CH}CH_2CH_2-$ | | |
| 8 | $-CH_2\underset{\underset{CH_3}{\mid}}{\overset{\overset{CH_3}{\mid}}{C}}CH_2-$ | | |

-continued

| Example Nos. | $-R^1-$ | $R^4$ | $R^5$ |
|---|---|---|---|
| 9 | $-(CH_2)_6-$ | | |
| 10 | $-CH_2CH_2CHCH_2CH_2-$ with $CH_3$ branch | | |
| 11 | $-(CH_2)_7-$ | | |
| 12 | $-CH_2CHCH_2-$ with $C_2H_5$ branch | | |
| 13 | $-(CH_2)_8-$ | | |
| 14 | $-CH_2CHCH_2-$ with $CH_2CH_2CH_3$ branch | | |
| 15 | $-CH_2CCH_2-$ with two $C_2H_5$ branches | | |
| 16 | $-CH-CHCH_2-$ with $H_5C_2$ and $CH_2CH_2CH_3$ branches | | |
| 17 | $-CHCH_2CH_2CH_2-$ with $CH_3$ branch | | |
| 18 | $-(CH_2)_9-$ | | |
| 19 | $-(CH_2)_{10}-$ | | |
| 20 | $-(CH_2)_{12}-$ | | |
| 21 | $-(CH_2)_{15}-$ | | |
| 22 | $-C_2H_4OC_2H_4OC_2H_4-$ | | |
| 23 | $-C_2H_4OC_2H_4-$ | | |
| 24 | $-CHCH_2OCHCH_2OCHCH_2-$ with three $CH_3$ branches | | |
| 25 | $-CHCH_2OCHCH_2-$ with two $CH_3$ branches | | |
| 26 | $-(CH_2)_3OCH_2CH_2O(CH_2)_3-$ | | |
| 27 | $-C_2H_4OSOOC_2H_4-$ | | |
| 28 | $-C_2H_4OCO(CH_2)_4COOC_2H_4-$ | | |
| 29 | $-C_2H_4OCO(CH_2)_8COOC_2H_4-$ | | |
| 30 | $-C_2H_4OCO(CH_2)_{10}COOC_2H_4-$ | | |
| 31 | $-C_2H_4OCO(CH_2)_{12}COOC_2H_4-$ | | |
| 32 | $-(CH_2)_3OCO(CH_2)_4COO(CH_2)_3-$ | | |
| 33 | $-(CH_2)_3OCO(CH_2)_6COO(CH_2)_3-$ | | |
| 34 | $-(CH_2)_3OCO(CH_2)_8COO(CH_2)_3-$ | | |
| 35 | $-CH_2CHOCO(CH_2)_3COOCHCH_2-$ with two $CH_3$ branches | | |
| 36 | $-CHCH_2OCO(CH_2)_8COOCH_2CH-$ with two $CH_3$ branches | | |
| 37 | $-(CH_2)_4OCOC_2H_4COO(CH_2)_4-$ | | |
| 38 | $-(CH_2)_4OCO(CH_2)_4COO(CH_2)_4-$ | | |
| 39 | $-C_2H_4N(Me)C_2H_4-$ | | |
| 40 | $-C_2H_4SO_2C_2H_4-$ | | |
| 41 | $-C_2H_4SO_2(CH_2)_4SO_2C_2H_4-$ | | |
| 42 | $-C_2H_4OCONH(CH_2)_6NHCOOC_2H_4-$ | | |
| 43 | $-C_2H_4OCOO(CH_2)_6OCOOC_2H_4-$ | | |
| 44 | $-CO(CH_2)_4CO-$ | | |
| 45 | $-CH_2COO(CH_2)_3OCOCH_2-$ | | |
| 46 | $-CH_2COO(CH_2)_4OCOCH_2-$ | | |
| 47 | $-CH_2COO(CH_2)_5OCOCH_2-$ | | |
| 48 | $-CH_2COO(CH_2)_6OCOCH_2-$ | | |
| 49 | $-CH_2COO(CH_2)_7OCOCH_2-$ | | |
| 50 | $-CH_2COO(CH_2)_8OCOCH_2-$ | | |
| 51 | $-CH_2COO(CH_2)_{12}OCOCH_2-$ | | |

-continued
| Example Nos. | —R¹— | R⁴ | R⁵ |
|---|---|---|---|
| 52 | —(CH₂)₃COO(CH₂)₄OCO(CH₂)₃— | | |
| 53 | —(CH₂)₃COO(CH₂)₅OCO(CH₂)₃— | | |
| 54 | —(CH₂)₃COO(CH₂)₆OCO(CH₂)₃— | | |
| 55 | —CH₂CONH(CH₂)₄NHCOCH₂— | | |
| 56 | —CH₂CONH(CH₂)₆NHCOCH₂— | | |
| 57 | 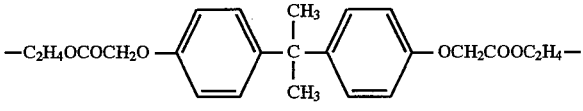 | | |
| 58 | 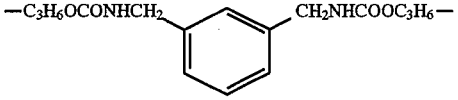 | | |
| 59 | 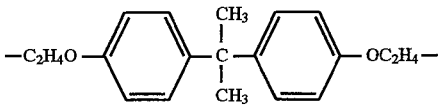 | | |
| 60 | 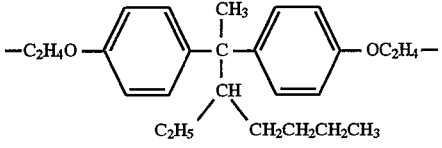 | | |
| 61 | 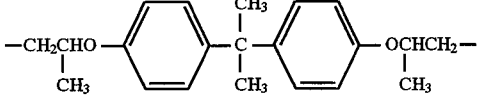 | | |
| 62 | 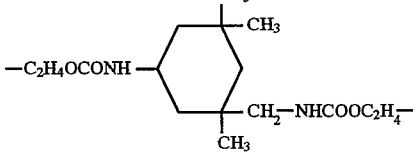 | | |
| 171 | —C₂H₄OCO(CH₂)₁₆COOC₂H₄— | | |
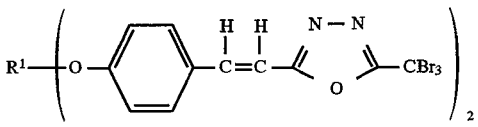
| | | | |
|---|---|---|---|
| 63 | —(CH₂)₇— | | |
| 64 | —CH₂CH₂CHCH₂CH₂—<br>            \|<br>           CH₃ | | |
| 65 | —(CH₂)₂OCO(CH₂)₆COO(CH₂)₂— | | |
| 66 | —(CH₂)₃OCO(CH₂)₆COO(CH₂)₃— | | |
| 67 | —CH₂COO(CH₂)₈OCOCH₂— | | |
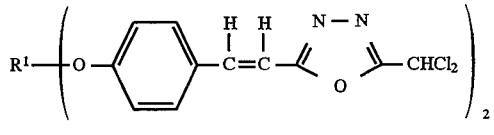
| | | | |
|---|---|---|---|
| 68 | —(CH₂)₆— | | |
| 69 | —CH₂CHCH₂—<br>          \|<br>       CH₂CH₃ | | |
| 70 | —(CH₂)₂OCO(CH₂)₆COO(CH₂)₂— | | |
| 71 | —(CH₂)₃OCO(CH₂)₆COO(CH₂)₃— | | |
| 72 | —CH₂COO(CH₂)₅OCOCH₂— | | |

-continued

| Example Nos. | —R¹— | R⁴ | R⁵ |
|---|---|---|---|
| 73 | —CH₂COO(CH₂)₆OCOCH₂— | | |
| 74 | —CH₂COO(CH₂)₈OCOCH₂— | | |

$$\left( R^1 - O - \underset{MeO}{\underset{|}{\bigcirc}} - CH=CH - \underset{O}{\overset{N-N}{\diagdown\diagup}} - CCl_3 \right)_2$$

| | | | |
|---|---|---|---|
| 75 | —(CH₂)₅— | | |
| 76 | —CH₂CH(CH₃)CH₂CH₂— | | |
| 77 | —CH₂C(CH₃)₂CH₂— | | |
| 78 | —(CH₂)₆— | | |
| 79 | —CH₂CH₂CH(CH₃)CH₂CH₂— | | |
| 80 | —CH₂CH(CH₂CH₂CH₃)CH₂— | | |
| 81 | —C₂H₄OCO(CH₂)₄COOC₂H₄— | | |
| 82 | —C₂H₄OCO(CH₂)₈COOC₂H₄— | | |
| 83 | —(CH₂)₃OCO(CH₂)₄COO(CH₂)₃— | | |
| 84 | —C₂H₄OC₂H₄OC₂H₄— | | |
| 85 | —CO(CH₂)₃CO— | | |
| 86 | —CO(CH₂)₄CO— | | |
| 87 | —CO(CH₂)₅CO— | | |
| 88 | —CO(CH₂)₆CO— | | |
| 89 | —CO(CH₂)₈CO— | | |
| 90 | —CH₂COO(CH₂)₃OCOCH₂— | | |
| 91 | —CH₂COO(CH₂)₄OCOCH₂— | | |
| 92 | —CH₂COO(CH₂)₅OCOCH₂— | | |
| 93 | —CH₂COO(CH₂)₆OCOCH₂— | | |
| 94 | —CH₂COO(CH₂)₇OCOCH₂— | | |
| 95 | —CH₂COO(CH₂)₈OCOCH₂— | | |
| 96 | —CH₂COO(CH₂)₁₂OCOCH₂— | | |
| 97 | —(CH₂)₃COO(CH₂)₄OCO(CH₂)₃— | | |
| 98 | —(CH₂)₃COO(CH₂)₅OCO(CH₂)₃— | | |
| 99 | —(CH₂)₃COO(CH₂)₆OCO(CH₂)₃— | | |
| 100 | —CH₂COOCH₂CH(CH₃)OCOCH₂— | | |
| 101 | —CH₂COOCH₂CH(CH₂CH₃)OCOCH₂— | | |
| 102 | —CH₂COOCH₂CH(CH₃)CH₂OCOCH₂— | | |
| 103 | —CH₂COOCH₂CH(CH₃)CH₂OCOCH₂— | | |
| 104 | —CH₂COOCH₂CH(CH₂CH₃)CH₂OCOCH₂— | | |
| 105 | —CH₂CONH(CH₂)₄NHCOCH₂— | | |
| 106 | —CH₂CONH(CH₂)₆NHCOCH₂— | | |
| 107 | —C₂H₄OCOCH₂O—⟨C₆H₄⟩—C(CF₃)₂—⟨C₆H₄⟩—OCH₂COOC₂H₄— | | |

-continued
| Example Nos. | —R¹— | R⁴ | R⁵ |
|---|---|---|---|
108 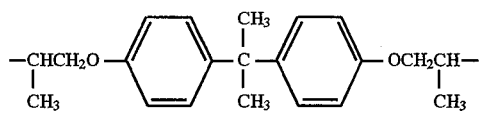
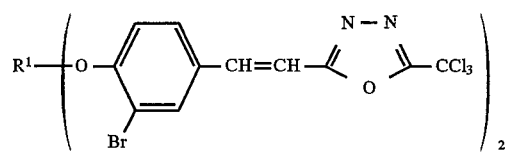
| 109 | —(CH₂)₅— |
| 110 | —C₂H₄OCO(CH₂)₈COOC₂H₄— |
| 111 | —CH₂COO(CH₂)₆OCOCH₂— |
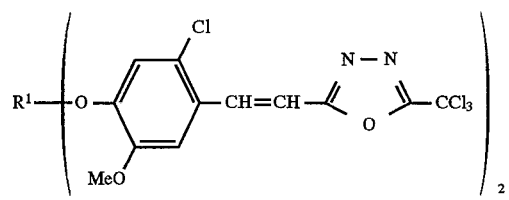
| 112 | —(CH₂)₅— |
| 113 | —C₂H₄OCO(CH₂)₁₀COOC₂H₄— |
| 114 | —CH₂COO(CH₂)₅OCOCH₂— |
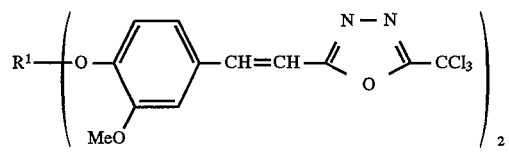
| 115 | —(CH₂)₅— |
| 116 | —C₂H₄OCO(CH₂)₁₀COOC₂H₄— |
| 117 | —CH₂COO(CH₂)₃OCOCH₂— |
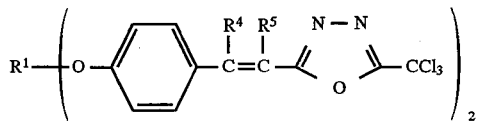
| 118 | —(CH₂)₄— | H | Me |
| 119 | —(CH₂)₃OCO(CH₂)₆COO(CH₂)₃— | H | Me |
| 120 | —C₂H₄OCO(CH₂)₄COOC₂H₄— | H | Ph |
| 121 | —CO(CH₂)₈CO— | H | Ph |
| 122 | —(CH₂)₃OCO(CH₂)₆COO(CH₂)₃— | Me | H |
| 123 | —(CH₂)₅— | Me | H |
| 124 | —CH₂COO(CH₂)₆OCOCH₂— | H | Me |
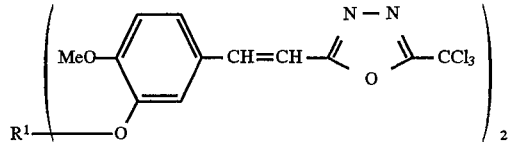
| 125 | —(CH₂)₅— |
| 126 | —CO(CH₂)₄CO— |
| 127 | —CH₂COO(CH₂)₅OCOCH₂— |
| 128 | —CH₂COO(CH₂)₆OCOCH₂— |
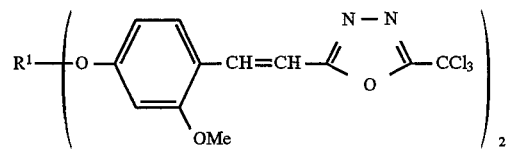

-continued
| Example Nos. | $-R^1-$ | $R^4$ | $R^5$ |
|---|---|---|---|
| 129 | $-(CH_2)_7-$ | | |
| 130 | $-C_2H_4OCO(CH_2)_8COOC_2H_4-$ | | |
| 131 | $-CH_2COO(CH_2)_6OCOCH_2-$ | | |
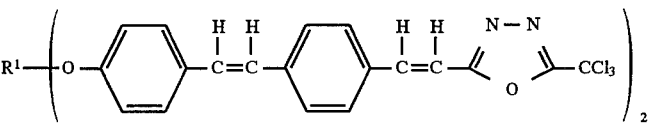
| | | | |
|---|---|---|---|
| 132 | $-(CH_2)_5-$ | | |
| 133 | $-(CH_2)_3OCO(CH_2)_{10}COO(CH_2)_3-$ | | |
| 134 | $-CH_2COO(CH_2)_6OCOCH_2-$ | | |
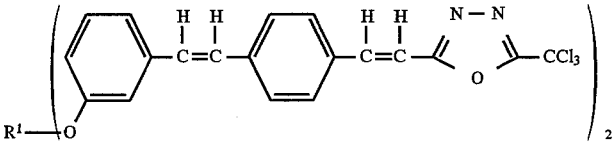
| | | | |
|---|---|---|---|
| 135 | $-(CH_2)_5-$ | | |
| 136 | $-C_2H_4OCO(CH_2)_{12}COOC_2H_4-$ | | |
| 137 | $-CH_2COO(CH_2)_5OCOCH_2-$ | | |
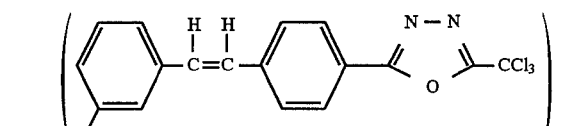
| | | | |
|---|---|---|---|
| 138 | $-(CH_2)_5-$ | | |
| 139 | $-C_2H_4OCO(CH_2)_8COOC_2H_4-$ | | |
| 140 | $-CH_2COO(CH_2)_5OCOCH_2-$ | | |
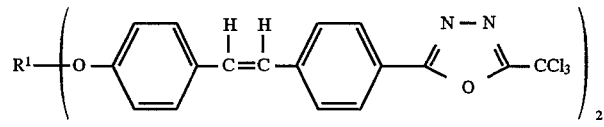
| | | | |
|---|---|---|---|
| 141 | $-(CH_2)_7-$ | | |
| 142 | $-(CH_2)_3OCO(CH_2)_4COO(CH_2)_3-$ | | |
| 143 | $-CH_2COO(CH_2)_5OCOCH_2-$ | | |
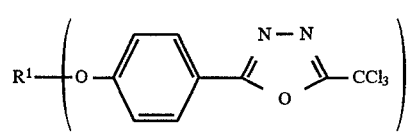
| | | | |
|---|---|---|---|
| 144 | $-(CH_2)_5-$ | | |
| 145 | $-C_2H_4OCO(CH_2)_{12}COOC_2H_4-$ | | |
| 146 | $-CH_2COO(CH_2)_3OCOCH_2-$ | | |
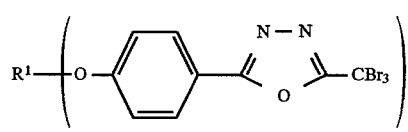
| | | | |
|---|---|---|---|
| 147 | $-(CH_2)_5-$ | | |
| 148 | $-C_2H_4OCO(CH_2)_8COOC_2H_4-$ | | |
| 149 | $-CH_2COO(CH_2)_5OCOCH_2-$ | | |
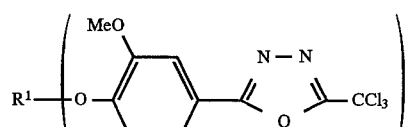
| | | | |
|---|---|---|---|
| 150 | $-(CH_2)_7-$ | | |

-continued
| Example Nos. | —R¹— | R⁴ | R⁵ |
|---|---|---|---|
| 151 | —(CH₂)₃OCO(CH₂)₄COO(CH₂)₃— | | |
| 152 | —CH₂COO(CH₂)₅OCOCH₂— | | |
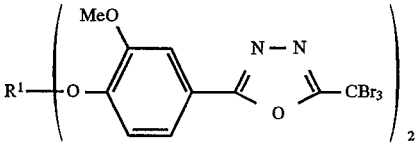
| | | | |
|---|---|---|---|
| 153 | —(CH₂)₅— | | |
| 154 | —C₂H₄OCO(CH₂)₁₂COOC₂H₄— | | |
| 155 | —CH₂COO(CH₂)₆OCOCH₂— | | |
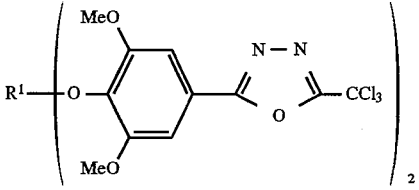
| | | | |
|---|---|---|---|
| 156 | —(CH₂)₄— | | |
| 157 | —C₂H₄OCO(CH₂)₆COOC₂H₄— | | |
| 158 | —CH₂COO(CH₂)₆OCOCH₂— | | |
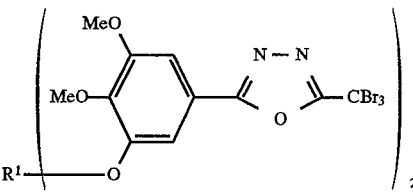
| | | | |
|---|---|---|---|
| 159 | —(CH₂)₅— | | |
| 160 | —(CH₂)₃OCO(CH₂)₈COO(CH₂)₃— | | |
| 161 | —CH₂COO(CH₂)₅OCOCH₂— | | |
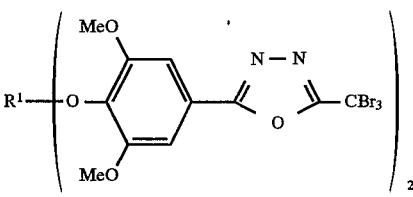
| | | | |
|---|---|---|---|
| 162 | —(CH₂)₃— | | |
| 163 | —C₂H₄OCO(CH₂)₁₀COOC₂H₄— | | |
| 164 | —CH₂COO(CH₂)₃OCOCH₂— | | |
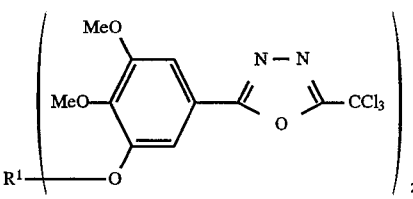
| | | | |
|---|---|---|---|
| 165 | —CH₂CH₂CHCH₂CH₂—<br>　　　　　CH₃ | | |
| 166 | —C₂H₄OCO(CH₂)₈COOC₂H₄— | | |
| 167 | —CH₂COO(CH₂)₆OCOCH₂— | | |
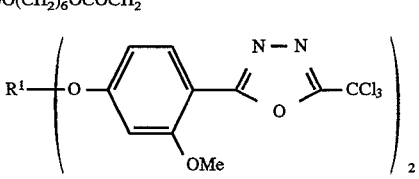
| | | | |
|---|---|---|---|
| 168 | —(CH₂)₅— | | |

-continued

| Example Nos. | —R¹— | R⁴ | R⁵ |
|---|---|---|---|
| 169 | —(CH₂)₃OCO(CH₂)₈COO(CH₂)₃— | | |
| 170 | —CH₂COO(CH₂)₅OCOCH₂— | | |

When a photosensitive bis(halomethyloxadiazole) compound according to the present invention contains a double bond in a molecular thereof, it may be either geometrical isomer. More specifically, substituents on the carbon atoms forming the double bond may be in the cis or trans conformation. However, it is preferable that they are mainly in the trans conformation. The proportion of the trans conformation to the cis conformation in the compound is preferbly in the range of 100:0 to 70:30.

The photosensitive bis(halomethyloxadiazole) compounds represented by general formula (1) can be synthesized according to a reaction formula (A), (B) or (C) described below:

Reaction formula (A)

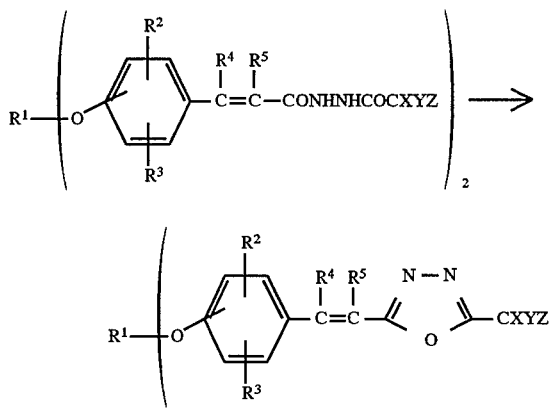

Reaction formula (B)

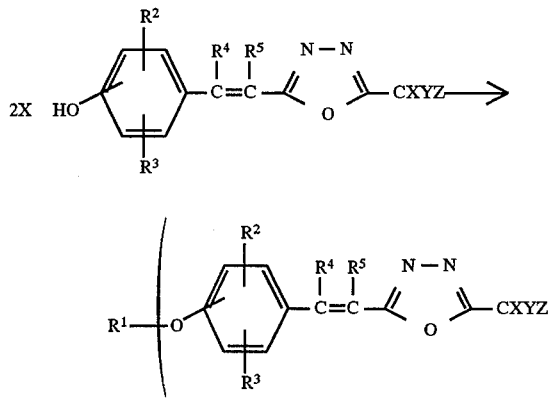

Reaction formula (C)

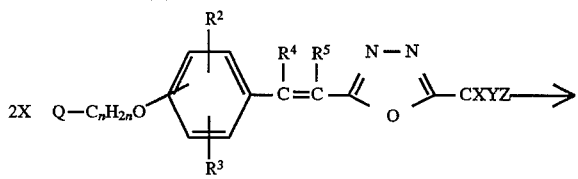

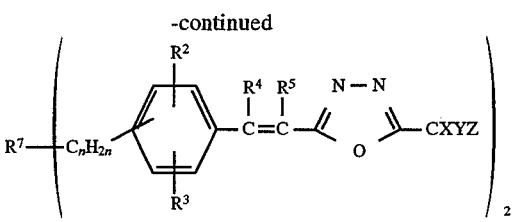

wherein Q represents a halogen atom, —OH group, —OL group (wherein L is an releasable group), —COOH group or so on.

Also, the photosensitive bis(halomethyloxadiazole) compounds represented by one of general formulae (2) to (4) can be synthesized according to the similar reaction.

More specifically, in the reaction formula (A), a bis(N-cinnamoyl-N'-haloacetylhydrazine) undergoes a ring closing reaction in a known manner to form a oxadiazole ring therein. In the reaction formulae (B) and (C), on the other hand, a halomethyloxadiazole having a reactive group which can react to dimerize is made to react with a linkage group-forming agent, thereby obtaining the intended bis compound. The group constituting the linkage part includes, e.g., an ether, ester, carbonate and urethane linkage group, and such a linkage can be easily formed by a known synthesis unit reaction corresponding thereto. The halomethyloxadiazoles which can be used as a starting material can be obtained according to the methods as described, e.g., in U.S. Pat. No. 4,212,970, JP-A-55-24113 and JP-A-02-1884.

The photosensitive bis(halomethyloxadiazole) compounds represented by one of the general formulae (1) to (4) are especially effective when they are used as a photoradical polymerization initiator in a photopolymerizable composition.

When the photosensitive bis(halomethyloxadiazole) compound represented by one of the general formulae (1) to (4) is contained in a photopolymerizable composition, the photopolymerizable composition preferably comprises a polymerizable compound having an ethylenically unsaturated bond and a photoradical polymerization initiator, and optionally a binder, and further a sensitizer, as needed.

Such a photopolymerizable composition is particularly useful for the photosensitive layer of a photosensitive printing plate, a color proof, a photoresist or so on.

One example of a photosensitive transfer sheet for preparing a color proof is described below.

The photosensitive transfer sheet of the present invention comprises a support having thereon a peeling layer and a photopolymerizable photosensitive resin layer in this order.

As for the material of a support, there can be used a material which is chemically and thermally stable, and has flexibility. The material may allow permeation of chemical rays therethrough, as needed. Specific examples of such a material include the various materials described, for example, in JP-A-47-41830, JP-A-48-9337 and JP-A-51-5101, such as cellulose acetate, polyvinyl chloride, polystyrene, polypropylene and so on. In particular, polyethylene terephthalate, polycarbonate and the heat-treated products thereof are preferred.

On the side of the support opposite the side for forming a peeling layer, a back layer made of a high molecular substance such as polyvinyl butyral, vinyl chloride-vinyl acetate copolymer, cellulose acetate, etc., may be provided for improving in workability and so on. The back layer may contain various additives such as a matting agent.

The peeling layer comprising an organic polymer for use in the present invention is provided on the support. Materials for the peeling layer can be appropriately selected from those materials which is known as useful for a peeling layer. Specific examples of such materials include alcohol-soluble polyamides, hydroxystyrene polymers, mixtures of alcohol-soluble polyamides with hydroxystyrene polymers, polyvinyl acetate, poly(meth)acrylates, polyvinyl chloride, polyvinyl butyrate, methylmethacrylate-acrylate copolymers, polyethylene-(meth)acrylic acid copolymers, cross-linked products of polyethylene-(meth)acrylic acid copolymers with metals, cellulose acetate butyrate, vinyl chloride-vinyl acetate copolymers, cellulose diacetate, cellulose triacetate, polyvinyl alcohol, and blends of partially esterified styrene-maleic anhydride copolymer resins with methoxymethlated nylon. Of these, mixtures of alcohol-soluble polyamides with hydroxystyrene polymers are preferred. The mixing ratio of an alcohol-soluble polyamide to a hydroxystyrene polymer in the mixture ranges preferably from 4:6 to 9:1 by weight in view of the releasability from the support under high humidity and the adhesiveness to an image-receiving sheet, another peeling layer, and a final support in a transfer step.

The peeling layer can be formed by dissolving the above described material in an appropriate solvent to prepare a coating solution, applying the coating solution to a support, and then drying. Various surfactants can be added to the coating solution as an agent for improving the surface condition. In particular, fluorine-containing surfactants are effective. The thickness of the peeling layer is generally in the range of from 0.1 to 20 µm, preferably in the range of from 0.2 to 5 µm, and particularly preferably in the range of from 0.3 to 3 µm.

Various known materials for photosensitive layers can be used for a material of a photopolymerizable photosensitive resin layer provided on the peeling layer. However, water-or alkali-developable photopolymerizable photosensitive resins are preferred.

The photopolymerizable photosensitive resin layer is generally comprises a monomer compound having a boiling point of 150° C. or higher under ordinary pressure and capable of forming a photopolymer by at least one addition-polymerizable group contained therein, such as a polyfunctional vinyl monomer or a vinylidene compound; an organic polymer binder; and a photopolymerization initiator which is activated by actinic rays; and optionally a thermal polymerization inhibitor. The photopolymerizable photosensitive resin layer of the present invention is characterized in particular by the photopolymerization initiator contained therein.

Examples of the vinyl monomer or vinylidene compound which can be used for the formation of the photopolymerizable photosensitive resin layer preferably include unsaturated esters of polyols, and particularly preferably, acrylic or methacrylic acid esters of polyols. Specific examples of such unsaturated esters include ethylene glycol diacrylate, glycerol triacrylate, polyacrylate, ethylene glycol dimethacrylate, 1,3-propanediol dimethacrylate, polyethylene glycol dimethacrylate, 1,2,4-butanetriol trimethacrylate, trimethylolethane triacrylate, pentaerythritol dimethacrylate, pentaerythritol trimethacrylate, pentaerythritol tetramethacrylate, pentaerythritol diacrylate, pentaerythritol triacrylate, pentaerythritol tetraacrylate, dipentaerythritol polyacrylate, 1,3-propanediol diacrylate, 1,5-pentanediol dimethacrylate, bisacrylate or bismethacrylate of polyethylene glycol having a molecular weight ranging from 200 to 400, and the like.

Unsaturated amides can also be used as the monomer compound. Examples thereof include unsaturated amides of acrylic or methacrylic acid containing an α,ω-diamine, and ethylenebismethacrylamide. Alkylene chain of the unsaturated amide may be linear or branched.

Suitable examples of the organic polymer binder include addition polymers having a side chain containing carboxylic acid groups, such as methacrylic acid copolymers (e.g., methylmethacrylate-methacrylic acid copolymers, ethylmethacrylate-methacrylic acid copolymers, butylmethacrylate-methacrylic acid copolymers, allylmethacrylate-methacrylic acid copolymers, ethylacrylate-methacrylic acid copolymers, ethylmethacrylate-styrene-methacrylic acid terpolymers, benzylmethacrylate-methacrylic acid copolymers, etc.); acrylic acid copolymers (e.g., ethylacrylate-acrylic acid copolymers, butylacrylate-acrylic acid copolymers, ethylacrylate-styrene-acrylic acid terpolymers, etc.); and, in addition, copolymers of itaconic acid, copolymers of crotonic acid, partially esterified copolymers of maleic acid, and acidic cellulose derivatives having a side chain containing a carboxylic acid group. However, the polymer binder for use in the present invention should not be construed as being limited to the above described examples.

These organic polymer binders may be used alone, or as a mixture of two or more thereof in an appropriate proportions. Such binders in admixture should have good compatibility with one another to the extent that the binders do not separate during preparing, coating and drying steps of the coating composition. The molecular weight of the organic polymer binders is in a wide range depending on the type of the polymer. However, the weight-average molecular weight is generally in the range of $5 \times 10^3$ to $2 \times 10^6$, and preferably in the range of $1 \times 10^4$ to $1 \times 10^6$.

A proper mixing ratio of the monomer compound to the organic polymer binder, though it depends on particular combination of the monomer compound and the organic polymer binder, ranges generally from 1:10 to 2:1 (by weight).

The photopolymerization initiator contained in the photopolymerizable photosensitive resin layer is a photopolymerization initiator comprising at least one photosensitive bis(halomethyloxadiazole) compound represented by one of the foregoing general formula (1), (2), (3) or (4).

In addition to the above described photosensitive bis (halomethyloxadiazole) compounds, other compounds which can initiate the photopolymerization of compounds containing an ethylenic unsaturated bond may be used as a photopolymerization initiator in the present photopolymerizable photosensitive resin layer. Examples of such compounds include the compounds described in *Light Sensitive Systems* written by J. Kosar, chapter 5, such as organic sulfur compounds, peroxides, redox compounds, azo and diazo compounds, substituted benzophenone derivatives, aromatic ketones, lophine dimer, and organic halogen compounds other than the present ones.

In the photopolymerizable photosensitive resin layer, the photopolymerization initiator is preferably contained in an amount of 0.01 to 20% by weight, more preferably 0.1 to 15% by weight, based on the weight of the monomer compounds. The optimum content thereof is in the range of 0.5 to 10% by weight. When the amount is less than 0.01% by weight, the sufficient sensitivity cannot be obtained; while when it is more than 20% by weight, whiteness in non-image areas is lowered. Moreover, the amount of the photosensitive bis(halomethyloxadiazole) compound(s) represented by general formula (1), (2), (3) or (4) is preferably not less than 40% by weight, more preferably not less than 50% by weight based on the total weight of the photosensitive initiators.

In the photopolymerizable photosensitive resin layer relating to the present invention, a reducing agent, e.g., an oxygen scavenger, a chain transfer agent of active hydrogen donor, and further other compounds to promote a polymerization in a manner of chain transfer reaction can be additionally used as an assistant agent for accelerating the polymerization. The oxygen scavenger include phosphine, phosphonates, phosphites, stannous salts and other compounds easily be oxidized by oxygen. Specific examples of such compounds include N-phenylglycine, trimethylbarbituric acid, N,N-dimethyl-2,6-diisopropylaniline, and N,N, N-2,4,6-pentamethylaniline. In addition, thiols, thioketones, trihalomethyl compounds, lophine dimer compounds, iodonium salts, sulfonium salts, azinium salts and organic peroxides are useful as a polymerization accelerator.

The thermal polymerization inhibitor include p-methoxyphenol, hydroquinone, alkyl- or aryl-substituted hydroquinones, t-butylcatechol, pyrogallol, naphthylamine, β-naphthol, phenothiazine, pyridine, nitrobenzene, o-toluquinone and aryl phosphites. However, the thermal polymerization inhibitor which can be used in the present invention should not be construed as being limited to these examples.

The thickness of the photopolymerizable photosensitive resin layer is generally in the range of 0.5 to 150 μm, and preferably in the range of 1 to 100 μm.

Details of materials and forming methods of the photosensitive resin layer are described, e.g., in U.S. Nos. 3,721,557, 3,920,677 and 4,482,625, Canadian Patent No. 1,045,872, JP-B-46-35682, JP-A-47-41830, and JP-A-48-93337.

When a coloring substance is used, the coloring substance may be contained in the photopolymerizable photosensitive resin layer, or a coloring layer containing the coloring substance may be provided separately. The coloring layer may be arranged above or below the photopolymerizable photosensitive resin layer. However, the coloring layer is preferably arranged below the photopolymerizable photosensitive resin layer for obtaining desired sensitivity of the photopolymerizable photosensitive resin layer in the imagewise exposure step. Examples of the coloring substance which can be used include known pigments and dyes. Pigments having a hue equivalent to a color ink (yellow, magenta, cyan and black) can be preferably used for color proofing for printings. Details of coloring pigments and the coloring layer are disclosed, e.g., in U.S. Pat. No. 4,482,625.

Further, a protective layer is preferably provided on the photopolymerizable photosensitive resin layer. The protective layer can be formed by coating a solution of high molecular compound, such as polyvinyl alcohol, polyvinyl acetate, methyl vinyl ether-maleic anhydride copolymer, polyvinyl pyrrolidone, gelatin, gum arabic, etc., and then drying the solution.

The photosensitive transfer sheet of the present invention thus prepared can be used for color proofing, e.g., by undergoing an operations according to a surprint method as described below:

1) A color separation mask is superposed upon a photosensitive transfer sheet, and thereto are exposed actinic rays (exposure step).

2) The resulting transfer sheet is processed with a developer to remove the unexposed area, to thereby form a separation image on the peeling layer (developing step).

3) The above-described steps 1) and 2) are repeated using another photosensitive transfer sheet, to thereby obtain two to four sheets of color proofing sheets having a separation image differently colored.

4) The color proofing sheet having a first color separation image is superposed upon an image-receiving sheet comprising a support and a photopolymerizable image-receiving layer so that the color separation image side may be brought into face-to-face contact with the image-receiving layer, and subsequently heat and pressure are applied thereto. Thus, the color proofing sheet is adhered to the image-receiving sheet in a condition such that the color separation image is embedded into the uncured image-receiving layer. Then, the support of the transfer sheet (temporary support) is removed therefrom, thus finishing the transfer of the image with the peeling layer (transfer step).

Further, each of the remaining color proofing sheets is subjected to the same operations as described above, wherein each of second and, if present, third and fourth color separation images is transferred into the same image-receiving sheet in turn so that it may be adjusted to the first color separation image. Thus, the image-receiving sheet has from two to four color separation images transferred to the image-receiving layer in a condition such that all the images are embedded therein.

5) The multicolor image-transferred image-receiving sheet is superposed on a white paper sheet so that the multicolor image may come into contact with the paper sheet, and then they are subjected to heat and pressure to adhere to each other.

6) The resulting material is subjected to overall exposure to actinic rays from the side of the support of the image-receiving sheet, to thereby photocure the photopolymerizable image-receiving layer.

7) The image having 2 to 4 colors are formed on the white paper by peeling the support of the image-receiving sheet (temporary support) therefrom. Fine unevenness may be formed on the surface of the image-receiving layer, as needed, by heating and pressing a mat film, etc. which is superposed onto the image-receiving layer.

Although the support onto which separation image is finally transferred is a white paper sheet in the above description, there can also be used other supports, such as various kinds of paper sheets, metal sheets, plastic films, glass plates and so on. Also, a multicolor image can be directly transferred to the final support without using any image-receiving sheet.

The color proofing sheets of from two to four colors which are obtained in the above described third step can also be used for color proof according to a overlay method by directly and precisely superposing the sheets upon one another.

The present invention will be described in detail with reference to the following examples. However, the invention should not be construed as being limited to these examples.

EXAMPLE 1

Synthesis of Compound 13:

Bis(N-substituted cinnamoyl-N'-trichloroacetylhydrazine) of formula (D) in an amount of 7.29 g and phosphorus oxychloride in an amount of 9.27 g were stirred for 2 hours at 105° C. The reaction mixture was poured into ice-cold water, and the precipitated crystals were filtered off, and washed with methanol and acetone. Thus, 5.21 g of Compound 13 was obtained. m.p. 148°–153° C.

Formula (D)

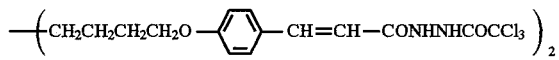

EXAMPLE 2

Synthesis of Compound 29:

Into a solution of 6.99 g of an oxadiazole compound of formula (E) and 2.39 g of sebacoyl chloride in 25 ml of acetonitrile, 2.20 g of triethylamine was dripped as the solution was cooled with ice. Then, the resulting mixture was stirred for 1 hour at room temperature. The reaction mixture obtained was poured into ice-cold water, and the crystals precipitated was filtered off, and recrystallized from acetonitrile. Thus, 7.01 g of Compound 29 was obtained. m.p. 96°–97° C.

Formula (E)

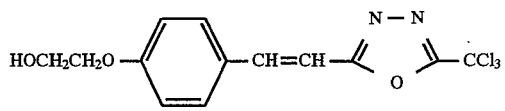

EXAMPLE 3

Synthesis of Compound 57:

Into a solution of 6.99 g of an oxadiazole compound of formula (E) and 3.81 g of 4,4'-isopropylidenediphenoxyacetyl chloride in 25 ml of acetonitrile, 2.20 g of triethylamine was dripped as the solution was cooled with ice. Then, the resulting mixture was stirred for 1 hour at room temperature. The reaction mixture obtained was poured into ice-cold water, and the crystals precipitated was filtered off, and recrystallized from acetonitrile. Thus, 8.56 g of Compound 57 was obtained. m.p. 70°–72° C.

EXAMPLE 4

Synthesis of Compound 42:

An oxadiazole compound of formula (E) in an amount of 6.99 g, 1.68 g of 1,6-hexamethylenediisocyanate and 0.1 g of dibutyltin diacetate were dissolved in 25 ml of tetrahydrofuran, and stirred for 3 hours at 40° C. The reaction mixture obtained was poured into ice-cold water, and the crystals precipitated was filtered off, and washed with methanol. Thus, 7.75 g of Compound 42 was obtained. m.p. 173°–176° C.

EXAMPLE 5

Synthesis of Compound 27:

Into a solution of 6.99 g of an oxadiazole compound of formula (E) and 1.0 g of thionyl chloride in 25 ml of acetonitrile, 2.20 g of triethylamine was dripped as the solution was cooled with ice. Then, the resulting mixture was stirred for 1 hour at room temperature. The reaction mixture obtained was poured into ice-cold water, and the crystals precipitated was filtered off, and recrystallized from acetonitrile. Thus, 2.84 g of Compound 27 was obtained. m.p. 154° C.

EXAMPLE 6

Synthesis of Compound 171:

Into a solution of 6.99 g of an oxadiazole compound of formula (E) and 3.51 g of 1,18-octadecanedionoic acid chloride in 25 ml of acetonitrile, 2.20 g of triethylamine was dripped as the solution was cooled with ice. Then, the resulting mixture was stirred for 1 hour at room temperature. The reaction mixture obtained was poured into ice-cold water, and the crystals precipitated was filtered off, and recrystallized from acetonitrile. Thus, 5.96 g of Compound 171 was obtained. m.p. 111°–112° C.

EXAMPLE 7

Synthesis of Compound 62:

An oxadiazole compound of formula (E) in an amount of 6.99 g, 2.80 g of isophorone diisocyanate and 0.1 g of dibutyltin diacetate were dissolved in 30 ml of tetrahydrofuran, and stirred for 8 hours at 40° C. The reaction mixture obtained was poured into ice-cold water, and the crystals precipitated was filtered off, and washed with acetonitrile. Thus, 4.10 g of Compound 62 was obtained. m.p. 180°–183° C.

EXAMPLE 8

Synthesis of Compound 34:

Into a solution of 7.27 g of an oxadiazole compound of formula (F) and 2.39 g of sebacoyl chloride in 25 ml of acetonitrile, 2.20 g of triethylamine was dripped as the solution was cooled with ice. Then, the resulting mixture was stirred for 1 hour at room temperature. The reaction mixture obtained was poured into ice-cold water, and the crystals precipitated was filtered off, and recrystallized from acetonitrile. Thus, 5.27 g of Compound 34 was obtained. m.p. 115°–117° C.

Formula (F)

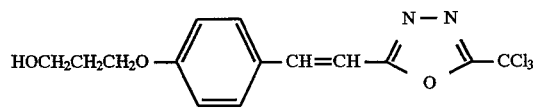

EXAMPLE 9

Synthesis of Compound 5:

Bis(N-substituted cinnamoyl-N'-trichloroacetylhydrazine) of formula (G) in an amount of 14.3 g and phosphorus oxychloride in an amount of 20.2 g were stirred for 2 hours at 105° C. The reaction mixture was poured into ice-cold water, and the precipitated crystals were filtered off, and washed with methanol and acetone. Thus, 5.38 g of Compound 5 was obtained. m.p. 149°–152° C.

Formula (G)

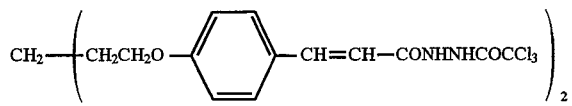

EXAMPLE 10

Synthesis of Compound 9:

Bis(N-substituted cinnamoyl-N'-trichloroacetylhydrazine) of formula (H) in an amount of 14.6 g and phosphorus oxychloride in the amount of 20.2 g were stirred for 2 hours at 105° C. The reaction mixture was poured into ice-cold water, and the precipitated crystals were filtered off, and washed with methanol and acetone. Thus, 6.81 g of Compound 9 was obtained. m.p. 184° C.

Formula (H)

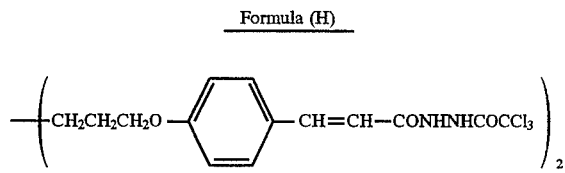

EXAMPLE 11

Synthesis of Compound 92:

An oxadiazole compound of formula (I) in an amount of 5.90 g, 1.70 g of 1,5-dibromopentane and 1.3 g of sodium hydrogen carbonate were dissolved in 15 ml of N,N-dimethylacetamide, and stirred for 3 hours at 90° C. The reaction mixture obtained was poured into ice-cold water, and the crystals precipitated was filtered off, and recrystallized from an ethyl acetate/methanol mixture. Thus, 3.34 g of Compound 92 was obtained. m.p. 62°–65° C.

Formula (I):

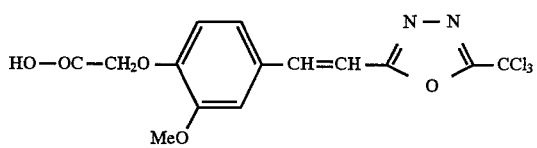

EXAMPLE 12

Synthesis of Compound 93:

An oxadiazole compound of formula (I) in an amount of 9.80 g, 3.05 g of 1,6-dibromohexane and 2.2 g of sodium hydrogen carbonate were dissolved in 25 ml of N,N-dimethylacetamide, and stirred for 3 hours at 90° C. The reaction mixture obtained was poured into ice-cold water, and the crystals precipitated was filtered off, and recrystallized from an ethyl acetate/methanol mixture. Thus, 7.15 g of Compound 93 was obtained. m.p. 109°–112° C.

EXAMPLE 13

Synthesis of Compound 128:

An oxadiazole compound of formula (J) in an amount of 9.80 g, 3.05 g of 1,6-dibromohexane and 2.2 g of sodium hydrogen carbonate were dissolved in 25 ml of N,N-dimethylacetamide, and stirred for 2 hours at 90° C. The reaction mixture obtained was poured into ice-cold water, and the crystals precipitated was filtered off, and recrystallized from an acetonitrile/methanol mixture. Thus, 7.01 g of Compound 128 was obtained. m.p. 123°–126° C.

Formula (J)

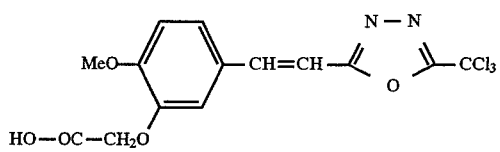

EXAMPLE 14

To a polyethylene terephthalate film (thickness: 100 μm) as a support, a coating solution having the following composition was applied, and then dried to form a peeling layer having a dry thickness of 0.5 μm.

| [Composition of Coating Solution for Peeling Layer] | |
|---|---|
| Alcohol-soluble polyamide (CM-8000, trade name, products of Toray Industries, Inc., Viscosity: 23 cps) | 5.4 g |
| Polyhydroxystyrene (Resin M, trade name, products of Maruzen Oil Co., Ltd.; Weight-average molecular weight: 5000) | 3.6 g |
| Methanol | 400 g |
| Methyl cellosolve | 100 g |

Photosensitive coating solutions of four colors, namely yellow (Y), magenta (M), cyan (C) and black (K), having the following compositions were respectively prepared as coating solutions for forming photopolymerizable photosensitive resin layers.

Coating Solution for Photopolymerizable Photosensitive Resin Layers:

| [Composition of Yellow Photosensitive Coating Solution] | |
|---|---|
| Benzylmethacrylate/methacrylic acid copolymer (ratio: 73/27 by mole, limiting viscosity number [η]: 0.12) | 60 g |
| Penetaerythritol tetraacrylate | 43.2 g |
| Photopolymerization initiator (Compound 5) | 2.16 g |
| Seika Fast Yellow H-7055 (trade name, products of Dainichiseika Colour & Chemicals Mfg. Co., Ltd.) | 9.4 g |
| Methylcellosolve acetate | 560 g |
| Methyl ethyl ketone | 280 g |
| Fluorine-containing surfactant (Florade FC-430, trade name, products of Sumitomo 3M Limited) | 1 g |
| [Composition of Magenta Photosensitive Coating Solution] | |
| Benzylmethacrylate/methacrylic acid copolymer (ratio: 73/27 by mole, limiting viscosity number [η]: 0.12) | 60 g |
| Pentaerythritol tetraacrylate | 43.2 g |
| Photopolymerization initiator (Compound 5) | 2.16 g |
| Seika Fast Carmine 1483 (trade name, products of Dainichiseika Colour & Chemicals Mfg. Co., Ltd.) | 5.2 g |
| Methylcellosolve acetate | 560 g |
| Methyl ethyl ketone | 280 g |
| Fluorine-containing surfactant (Florade FC-430, trade name, products of Sumitomo 3M Limited) | 1 g |
| [Composition of Cyan Photosensitive Coating Solution] | |
| Benzylmethacrylate/methacrylic acid copolymer (ratio: 73/27 by mole, limiting viscosity number [η]: 0.12) | 60 g |
| Pentaerythritol tetraacrylate | 43.2 g |

-continued

| | |
|---|---|
| Photopolymerization initiator (Compound 5) | 2.16 g |
| Cyanine Blue 4920 | 5.6 g |
| (trade name, products of Dainichiseika Colour & Chemicals Mfg. Co., Ltd.) | |
| Methylcellosolve acetate | 560 g |
| Methyl ethyl ketone | 280 g |
| Fluorine-containing surfactant | 1 g |
| (Florade FC-430, trade name, products of Sumitomo 3M Limited) | |

[Composition of Black Photosensitive Coating Solution]

| | |
|---|---|
| Benzylmethacrylate/methacrylic acid coploymer | 60 g |
| (ratio: 73/27 by mole, limiting viscosity number [η]: 0.12) | |
| Pentaerythritol tetraacrylate | 43.2 g |
| Photopolymerization initiator (Compound 5) | 2.16 g |
| Mitsubishi Carbon Black MA-100 | 6.6 g |
| (trade name, products of Dainichiseika Colour & Chemicals Mfg. Co., Ltd.) | |
| Methylcellosolve acetate | 560 g |
| Methyl ethyl ketone | 280 g |
| Fluorine-containing surfactant | 1 g |
| (Florade FC-430, trade name, products of Sumitomo 3M Limited) | |

The photosensitive coating compositions of these four colors were applied to the foregoing four separate support films which were each having the above described peeling layer coated thereon, and dried to form photopolymerizable photosensitive resin layers having the dry thickness of 2.4 μm on the respective peeling layers.

Separately, a coating solution having the following composition was prepared, applied to each of the polymerizable photosensitive resin layers of the four colors, and dried to form a protective layer having a dry thickness of 1.5 μm.

[Composition of Coating Solution for Protective Layer]

| | |
|---|---|
| Polyvinyl alcohol | 60 g |
| (GL-05, trade mark, products of The Nippon Synthetic Chemical Industry Co., Ltd.) | |
| Water | 970 g |
| Methanol | 30 g |

Thus, there were obtained photosensitive transfer sheets of four different colors (negative working colored photosensitive sheets) each comprising a support, a peeling layer, a Photopolymerizable photosensitive resin layer and a protective layer, which were arranged in this order.

EXAMPLES 15 TO 62

Other 48 sets of photosensitive transfer sheets of four different colors were prepared in the same manner as in Example 1, except that the Photopolymerization initiator used in the coating solution for forming the polymerizable photosensitive resin layers was changed from Compound (5) to the same mols of the compound set forth in Table 1, respectively.

TABLE 1

Photopolymerization Initiator added

| Example No. | Compound No. |
|---|---|
| 15 | 9 |
| 16 | 10 |
| 17 | 13 |
| 18 | 16 |

TABLE 1-continued

Photopolymerization Initiator added

| Example No. | Compound No. |
|---|---|
| 19 | 22 |
| 20 | 27 |
| 21 | 29 |
| 22 | 34 |
| 23 | 42 |
| 24 | 46 |
| 25 | 56 |
| 26 | 57 |
| 27 | 58 |
| 28 | 61 |
| 29 | 62 |
| 30 | 63 |
| 31 | 71 |
| 32 | 79 |
| 33 | 82 |
| 34 | 86 |
| 35 | 88 |
| 36 | 90 |
| 37 | 92 |
| 38 | 93 |
| 39 | 95 |
| 40 | 99 |
| 41 | 100 |
| 42 | 106 |
| 43 | 108 |
| 44 | 123 |
| 45 | 125 |
| 46 | 126 |
| 47 | 128 |
| 48 | 129 |
| 49 | 132 |
| 50 | 135 |
| 51 | 139 |
| 52 | 146 |
| 53 | 150 |
| 54 | 152 |
| 55 | 153 |
| 56 | 165 |
| 57 | 167 |
| 58 | 5 + 82 |
| 59 | 9 + 82 |
| 60 | 10 + 79 |
| 61 | 29 + 125 |
| 62 | 61 + 126 |

In each of Examples 58 to 62, the two compounds set forth were mixed in the same amount (by weight).

EXAMPLE 63

Another set of photosensitive transfer sheets of four different colors was prepared in the same manner as in Example 14, except that the composition of the coating solution for the peeling layer was changed to the following composition.

[Coating Solution for Peeling Layer]

| | |
|---|---|
| Alcohol-soluble polyamide | 7.2 g |
| (CM-8000, trade name, products of Toray Industries, Inc., Viscosity: 23 cps) | |
| Polyhydroxystyrene | 1.8 g |
| (Resin M, trade name, products of Maruzen Oil Co., Ltd.; Average molecular weight: 5000) | |
| Methanol | 400 g |
| Methyl cellosolve | 100 g |

EXAMPLES 64 TO 76

Other 13 sets of photosensitive transfer sheets of four different colors were prepared in the same manner as in Example 63, except that the photopolymerization initiator used in the coating solution for forming the polymerizable photosensitive resin layer was changed from Compound (5) to the same mols of the compound set forth in Table 2, respectively.

TABLE 2

| Photopolymerization Initiator added | |
|---|---|
| Example No. | Compound No. |
| 64 | 9 |
| 65 | 10 |
| 66 | 29 |
| 67 | 34 |
| 68 | 42 |
| 69 | 61 |
| 70 | 82 |
| 71 | 88 |
| 72 | 90 |
| 73 | 92 |
| 74 | 93 |
| 75 | 95 |
| 76 | 100 |

Comparative Example 1

Still another set of photosensitive transfer sheets of four different colors was prepared in the same manner as in Example 14, except that the photopolymerization initiator used in the coating solution for forming the polymerizable photosensitive resin layer was changed from Compound (5) to the compound represented by the following formula (K), in which the molar amount of the compound used was two times the amount of Compound (5) in Example 14:

Formula (K)

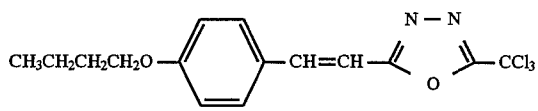

Comparative Example 2

A further set of photosensitive transfer sheets of four different colors was prepared in the same manner as in Example 14, except that the photopolymerization initiator used in the coating solution for forming the polymerizable photosensitive resin layer was changed from Compound (5) to the compound represented by the following formula (L), in which the molar amount of the compound used was two times the amount of Compound (5) in Example 14:

Formula (L)

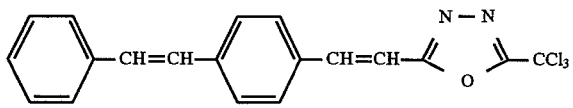

Comparative Example 3

A further set of photosensitive transfer sheets of four different colors was prepared in the same manner as in Example 63, except that the photopolymerization initiator used in the coating solution for forming the polymerizable photosensitive resin layer was changed from Compound (5) to the compound represented by the foregoing formula (K), in which the molar amount of the compound used was two times the amount of Compound (5) in Example 14.

Evaluation of Photosensitive Transfer Sheets

Each set of the photosensitive transfer sheets prepared in Examples and Comparative Examples was subjected to a color stain test as described below:

Corresponding color separation masks were superposed upon each of the four photosensitive transfer sheets having a different color using register pins. The transfer sheets were imagewise exposed with a 1 kW ultra-high pressure mercury lamp, P-607 FW (made by Dainippon Screen Mfg. Co., Ltd.) for 60 seconds, and then processed in an automatic processor (ColorArt Processor CA-600P, trade name, made by Fuji Photo Film Co., Ltd.) at 31° C. for 22 seconds with using a 5-fold diluted solution of Color Art Developer CA-1 (trade name, products of Fuji Photo Film Co., Ltd.). Thus, for each Example and comparative Example, four transfer sheet of different color were obtained which were faithfully reproduced from the color separation masks.

Separately, a coating solution having the composition described below was prepared and applied to a biaxially stretched polyethylene terephthalate film having a thickness of 100 μm, and was dried to form an image-receiving layer having a dry thickness of 20 μm. Thus image-receiving sheets was prepared.

| [Composition of Coating Solution for Image-Receiving Layer] | |
|---|---|
| Methylmethacrylate polymer (average molecular weight: 100,000, produced by Wako Pure Chemical Industries, Ltd.) | 90 g |
| Pentaerythritol tetraacrylate | 90 g |
| 2,2-Dimethoxy-2-phenylacetophenone | 3.18 g |
| p-Methoxyphenol | 0.09 g |
| Methyl ethyl ketone | 220 g |

Subsequently, a black photosensitive transfer sheet (first color) was first superposed upon the image-receiving sheet so as to bring the image side of the transfer sheet into contact with the film surface of the image-receiving material, and the sheets were laminated using a Color Art Transfer Press, CA-600T (made by Fuji Photo Film Co., Ltd.). Thereafter, the support of the photosensitive transfer sheet was peeled, to thereby transfer a black image into the image-receiving sheet. Further, the three remaining photosensitive transfer sheets each having a different color were, one by one, positioned and successively transferred to the same sheet, to obtained an image-receiving sheet having a four-colored halftone dot image.

Subsequently, the image-receiving sheet having transferred thereto a four-colored image was superposed upon an art paper sheet (final support), and the sheets were laminated using the above described transfer press. Then, the laminated sheet was subjected to overall exposure from the side of the image-receiving sheet with a Roomlight Printer, P-607 FW (made by Dainippon Screen Mfg. Co., Ltd., equipped with a 1 kW ultra-high pressure mercury lamp) for 120 seconds. Subsequently, the support of the image-receiving sheet was removed to form a final image on the art paper sheet (color proof).

Non-image areas of the thus obtained color proof having the four-color halftone image formed by the foregoing transfer operations was examined with a reflection densitometer, RD 918 (made by Macbeth Co., Ltd., wherein B-filter was used).

Separately, a reference sample was prepared as follows: The image-receiving sheet without any transferred images was superposed on an art paper sheet (the same sheet as used above as the final support), and the sheets were laminated using the above described Color Art Transfer Press (CA-600T, made by Fuji Photo Film Co., Ltd.). Then, the laminated sheet was subjected to overall exposure from the side of the image-receiving sheet using a Roomlight Printer, P-607 FW (made by Dainippon Screen Mfg. Co., Ltd., equipped with a 1 kW ultra-high pressure mercury lamp) for 120 seconds. Subsequently, the support of the image-receiving sheet was removed to form an image receiving layer on the art paper sheet.

The thus obtained reference sample (image-receiving layer having no image with an art paper sheet) was examined for color stain with a reflection densitometer, RD 918 (made by Macbeth Co., Ltd., wherein B-filter was used).

The color stain in the non-image area of each color proof sample was evaluated by the remainder found by taking the color stain data of the reference sample from the reflection density determined in the non-image area of each color proof-sample. The evaluation results are shown in Table 3.

TABLE 3

| Example No. | Color Stain |
|---|---|
| 14 | 0.010 |
| 15 | 0.010 |
| 16 | 0.010 |
| 17 | 0.010 |
| 18 | 0.010 |
| 19 | 0.010 |
| 20 | 0.010 |
| 21 | 0.010 |
| 22 | 0.010 |
| 23 | 0.010 |
| 24 | 0.010 |
| 25 | 0.010 |
| 26 | 0.010 |
| 27 | 0.010 |
| 28 | 0.010 |
| 29 | 0.010 |
| 30 | 0.010 |
| 31 | 0.010 |
| 32 | 0.010 |
| 33 | 0.010 |
| 34 | 0.010 |
| 35 | 0.010 |
| 36 | 0.010 |
| 37 | 0.010 |
| 38 | 0.010 |
| 39 | 0.010 |
| 40 | 0.010 |
| 41 | 0.010 |
| 42 | 0.010 |
| 43 | 0.010 |
| 44 | 0.020 |
| 45 | 0.010 |
| 46 | 0.010 |
| 47 | 0.010 |
| 48 | 0.010 |
| 49 | 0.020 |
| 50 | 0.020 |
| 51 | 0.020 |
| 52 | 0.010 |
| 53 | 0.010 |
| 54 | 0.010 |
| 55 | 0.010 |
| 56 | 0.010 |
| 57 | 0.010 |
| 58 | 0.010 |
| 59 | 0.010 |

TABLE 3-continued

| | Color Stain |
|---|---|
| 60 | 0.010 |
| 61 | 0.020 |
| 62 | 0.010 |
| 63 | 0.010 |
| 64 | 0.010 |
| 65 | 0.010 |
| 66 | 0.010 |
| 67 | 0.010 |
| 68 | 0.010 |
| 69 | 0.010 |
| 70 | 0.010 |
| 71 | 0.010 |
| 72 | 0.010 |
| 73 | 0.010 |
| 74 | 0.010 |
| 75 | 0.010 |
| 76 | 0.010 |
| Compara. Example No. | |
| 1 | 0.100 |
| 2 | 0.050 |
| 3 | 0.090 |

As can be seen from Table 3, all of the photosensitive transfer sheets prepared in accordance with the present invention generates considerably reduced color stain in their respective non-image areas. Therefore, a color proof prepared with the photosensitive transfer sheet is excellent with exhibiting a markedly effect on improvement in similarity of printed matters to originals.

Moreover, the photosensitive bis(halomethyloxadiazole) compounds of the present invention are novel compounds which can produce free radicals when exposed to light, and are useful in the field of recording materials, such as a photosensitive protective films, a printing plate, a photoresist, a color proof and the like.

While the invention has been described in detail and with reference to specific examples thereof, it will be apparent to one skilled in the art that various changes and modifications can be made therein without departing from the spirit and scope thereof.

What is claimed is:

1. A photosensitive transfer sheet comprising a support having thereon (a) a peeling layer containing an organic polymer and (b) a photopolymerizable photosensitive resin layer containing a photosensitive resin and a photopolymerization initiator, in this order, wherein said photopolymerization initiator comprises at least one photosensitive bis (halomethyloxadiazole) compound represented by one of the following general formulae (1) to (4):

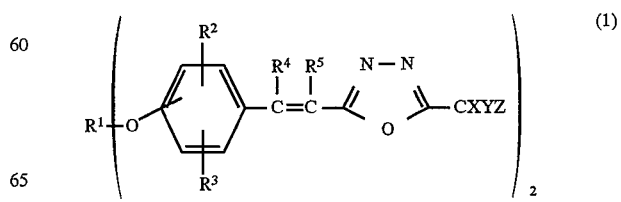

-continued

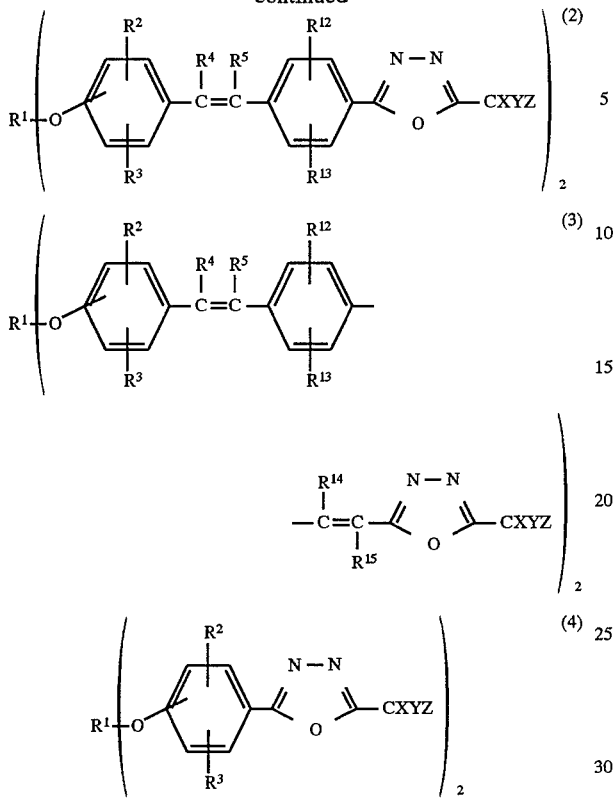

wherein $R^1$ represents —CO—$R_6$—CO—, —$C_nH_{2n}$—, or —$C_nH_{2n}$—$R^7$—$C_nH_{2n}$—; n represents an integer of from 1 to 20; $R^2$, $R^3$, $R^{12}$ and $R^{13}$ are the same or different, and each represents a hydrogen atom, an alkyl group containing 1 to 10 carbon atoms, an alkoxy group containing 1 to 10 carbon atoms, an acyloxy group containing 2 to 10 carbon atoms, or a halogen atom; $R^4$, $R^5$, $R^{14}$ and $R^{15}$ are the same or different, and each represents a hydrogen atom, an alkyl group containing 1 to 10 carbon atoms, an unsubstituted phenyl group, or a substituted phenyl group substituted with an alkyl or alkoxy group containing 1 to 6 carbon atoms or a halogen atom; X, Y and Z are the same or different, and each represents a hydrogen atom or a halogen atom, providing that all of X, Y and Z cannot be hydrogen atoms simultaneously; $R^6$ represents —$C_mH_{2m}$— or —$OC_mH_{2m}O$—; m represents an integer of from 2 to 20; $R^7$ represents —O—, —S—, —$N(R^8)$—, —$SO_2$—, —O—SO—O—, —O—CO—$R^9$—CO—O—, —$SO_2$—$R^9$—$SO_2$—, —CO—$R^9$—CO—, or —O—$R^{10}$—O—; $R^8$ represents an alkyl group containing 1 to 10 carbon atom, an unsubstituted phenyl group, or a substituted phenyl group substituted with an alkyl or alkoxy group containing 1 to 6 carbon atoms or a halogen atom; $R^9$ represents —$C_lH_{2l}$—, —$C_lH_{2l}O$—$R^{11}$—$OC_lH_{2l}$—, —$NHC_kH_{2k}NH$—, —$NHC_kH_{2k-2}NH$—, —$NHCH_2$—$C_6H_4$—$CH_2NH$—, —$OC_kH_{2k}O$—, or —$C_6H_4$—; l represents an integer of from 1 to 20; k represents an integer of from 2 to 20; $R^{10}$ represents —$C_pH_{2p}$— or —$C_pH_{2p}$—O—$R^{11}$—$OC_pH_{2p}$—; p represents an integer of from 2 to 20; $R^{11}$ represents —$C_6H_4$—$C_qH_{2q}$—$C_6H_4$—, —$C_6H_4$—S—$C_6H_4$—, $C_6H_4$—$SO_2$—$C_6H_4$—, —$C_6H_4$—, —$C_6H_4$—O—$C_6H_4$—, —$C_6H_4$—$C(CF_3)_2$—$C_6H_4$— or —$C_6H_4$—$C_6H_4$; and q represents an integer of from 2 to 10.

2. A photosensitive composition comprising a photosensitive resin and a photopolymerization initiator, wherein the photopolymerization initiator comprises at least one photosensitive bis(halomethyloxadiazole) compound represented by one of the following general formulae (1) to (4):

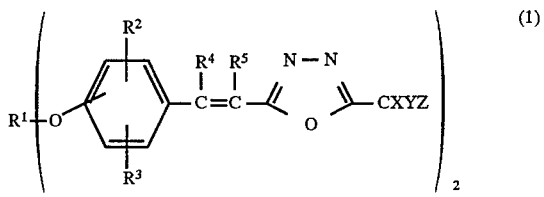

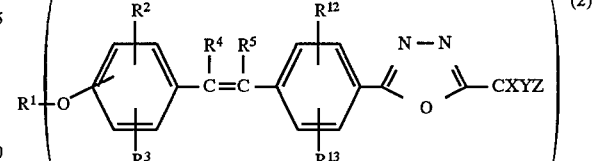

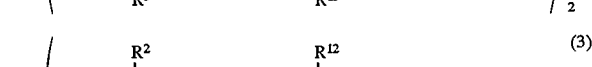

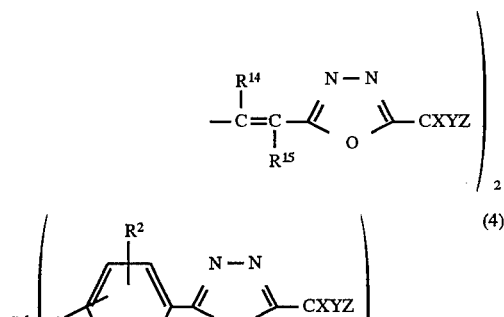

wherein $R^1$ represents —CO—$R^6$—CO—, —$C_nH_{2n}$—, or —$C_nH_{2n}$—$R^7$—$C_nH_{2n}$—; n represents an integer of from 1 to 20; $R^2$, $R^3$, $R^{12}$ and $R^{13}$ are the same or different, and each represents a hydrogen atom, an alkyl group containing 1 to 10 carbon atoms, an alkoxy group containing 1 to 10 carbon atoms, an acyloxy group containing 2 to 10 carbon atoms, or a halogen atom; $R^4$, $R^5$, $R^{14}$ and $R^{15}$ are the same or different, and each represents a hydrogen atom, an alkyl group containing 1 to 10 carbon atoms, an unsubstituted phenyl group, or a substituted phenyl group substituted with an alkyl or alkoxy group containing 1 to 6 carbon atoms or a halogen atom; X, Y and Z are the same or different, and each represents a hydrogen atom or a halogen atom, provided that all of X, Y and Z are not hydrogen atoms simultaneously; $R^6$ represents —$C_mH_{2m}$— or —$OC_mH_{2m}O$—; m represents an integer of from 2 to 20; $R^7$ represents —O—, —S—, —$N(R^8)$—, —$SO_2$—, —O—SO—O—, —O—CO—$R^9CO$—O—, —$SO_2$—$R^9$—$SO_2$—, —CO—$R^9$—CO—, or —O—$R^{10}$—O—; $R^8$ represents an alkyl group containing 1 to 10 carbon atoms, an unsubstituted phenyl group, or a substituted phenyl group substituted with an alkyl or alkoxy group containing 1 to 6 carbon atoms or a halogen atom; $R^9$ represents $-C_lH_{2l}-$, $-C_lH_{2l}O-R^{11}-OC_lH_{2l}-$, $-NHC_kH_{2k}NH-$, $-NHC_kH_{2k-2}NH-$, $-NHCH_2-C_6H_4-CH_2NH-$, $-OC_kH_{2k}O-$, or $-C_6H_4-$; l represents an integer or from 1 to 20; k represents an integer of from 2 to 20; $R^{10}$ represents $-C_pH_{2p}-$ or $-C_pH_{2p}-O-R^{11}-OC_pH_{2p}-$; p represents an integer of from 2 to 20; $R^{11}$ represents $-C_6H_4-C_qH_{2q}-C_6H_4-$, $-C_6H_4-S-C_6H_4-$, $-C_6H_4-SO_2-C_6H_4-$, $-C_6H_4-$, $-C_6H_4-O-C_6H_4-$, $-C_6H_4-C(CF_3)_2-C_6H_4-$ or $-C_6H_4-C_6H_4-$; and q represents an integer of from 2 to 10.

* * * * *